United States Patent
Heinrich et al.

(10) Patent No.: US 8,546,406 B2
(45) Date of Patent: *Oct. 1, 2013

(54) HETEROCYCLIC COMPOUNDS AS METAP-2 INHIBITORS

(75) Inventors: Timo Heinrich, Gross-Umstadt (DE); Frank Zenke, Darmstadt (DE); Mireille Krier, Darmstadt (DE); Kai Schiemann, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 5 days.

This patent is subject to a terminal disclaimer.

(21) Appl. No.: 13/145,422

(22) PCT Filed: Dec. 22, 2009

(86) PCT No.: PCT/EP2009/009218
§ 371 (c)(1),
(2), (4) Date: Jul. 20, 2011

(87) PCT Pub. No.: WO2010/083870
PCT Pub. Date: Jul. 29, 2010

(65) Prior Publication Data
US 2011/0281859 A1    Nov. 17, 2011

(30) Foreign Application Priority Data
Jan. 20, 2009 (DE) .......................... 10 2009 005 193

(51) Int. Cl.
A61K 31/519 (2006.01)
A61K 31/52 (2006.01)
C07D 487/14 (2006.01)
C07D 487/22 (2006.01)

(52) U.S. Cl.
USPC ................ 514/259.31; 514/259.3; 514/263.1; 544/262

(58) Field of Classification Search
USPC ............... 514/259.3, 259.31, 263.1; 544/262
See application file for complete search history.

(56) References Cited

U.S. PATENT DOCUMENTS
3,037,980 A * 6/1962 Hitchings et al. ............. 544/280

FOREIGN PATENT DOCUMENTS
FR          2 448 542      *  2/1979
WO     WO 2007/017069 A1     2/2007

OTHER PUBLICATIONS

Reiter, Jozsef. on Triazoles. VIII [1]. The Reaction of 5-Amino-1,2,4-Triazoles with Ethyl 2-Cyano-3-Ethoxyacrylate and 2-Cyano-3-Ethoxyacrylonitrile [2]. Journal of Heterocyclic Chemistry. (1987), 24(4), 1149-54.*
International Search Report of PCT/EP2009/009218 (Jun. 3, 2010).

* cited by examiner

*Primary Examiner* — Samantha Shterengarts
(74) *Attorney, Agent, or Firm* — Millen, White, Zelano & Branigan, P.C.

(57) ABSTRACT

Compounds of the formula I, in which D, X, Y, Z, R and $R^1$ have the meanings indicated in Claim 1, are inhibitors of methionine aminopeptidase and can be employed for the treatment of tumors.

4 Claims, No Drawings

HETEROCYCLIC COMPOUNDS AS METAP-2 INHIBITORS

The invention relates to compounds of the formula I

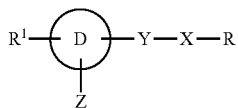

in which

denotes pyrrolidinyl, pyrazolyl, pyrazolinyl, pyrazolidinyl, imidazolyl, imidazolinyl, imidazolidinyl, 2-oxa-5-azabicyclo[2.2.1]hept-5-yl, morpholinyl or N, Z denotes imidazopyrimidinyl, imidazotriazinyl, triazolopyrimidinyl, triazolotriazinyl, triazolopyridazinyl, tetrazolopyrimidinyl, tetrazolotriazinyl, tetrazolopyridazinyl, pyrazolopyridazinyl or pyrrolopyrimidinyl, each of which is unsubstituted or monosubstituted by $R^2$ where Z is bonded to a nitrogen of the radical D, $R^1$ denotes H, Hal, =O, OH, $NH_2$, A or COA, $R^2$ denotes H, A, Hal, $NH_2$, $SCH_3$, OH or =O, $R^6$ denotes H or alkyl having 1-6 C atoms, X denotes $O(CH_2)_r$, NH, NA, OC(=O), $NHSO_2$ or is absent, Y denotes CH=CH, $(CH_2)_n$ or is absent, R denotes H, Ar, Het or $Carb^1$, Ar denotes phenyl, naphthyl or biphenyl, each of which is unsubstituted or mono-, di-, tri-, tetra- or pentasubstituted by Hal, A, $OR^6$,
$(CH_2)_mN(R^6)_2$, $NO_2$, $[C(R^6)_2]_rCN$, $(CH_2)_mCOOR^6$, $CON(R^6)_2$,
$NR^6COA$, $NR^6SO_2A$, $COR^6$, $SO_2N(R^6)_2$, $S(O)_qA$, $SO_2OH$,
$CH=CH—CONH(CH_2)_pOH$, NHCONH-Het, NHCONHA,
$(CH_2)_mAr^1$, $O(CH_2)_mAr^1$, $O(CH_2)_mHet^2$, $O(CH_2)_mCOOR^6$,

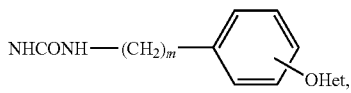

$(CH_2)_mHet$, $CH_2NH[(CH_2)_2O]_q[(CH_2)_2O]_q(CH_2)_pNH_2$, $CH_2N(COA)CH_2CH(OH)CH_2OH$,
$CH_2NH(CH_2)_qHet$, $CH_2N(COA)(CH_2)_qHet$, $CH_2N(CHO)(CH_2)_qHet$,
COHet, $NHCOCH[(CH_2)_mCOOA]NHCOO(CH_2)_mAr^1$,
$NHCOCH[(CH_2)_mCONH_2]NHCOOA$,
$NHCOCH[(CH_2)_mCOOH]NHCOOH$,
$NHCOCH[(CH_2)_mHet^2]NHCOOA$,
$NHCOCH[(CH_2)_mHet^2]NH_2$,
$NHCOCH[(CH_2)_mCONH_2]NH_2$, $CH=CH—COOR^6$ and/or
$CH=CH—CON(R^6)_2$, Het denotes a mono-, bi- or tricyclic saturated, unsaturated or aromatic heterocycle having 1 to 4 N, and/or O and/or S atoms which is unsubstituted or mono-, di- or trisubstituted by Hal, A,
$(CH_2)_mOR^6$, $(CH_2)_mN(R^6)_2$, $NO_2$, $(CH_2)_mCN$, $(CH_2)_mCOOR^6$,
$CONH(CH_2)_mCOOH$, $CONH(CH_2)_mHet^2$, $CO(CH_2)_mN(R^6)_2$,
$CO(CH_2)_mNH(CH_2)_rCOOA$, $COO(CH_2)_mAr^1$,
$(CH_2)_rCONH(CH_2)_mAr^1$, $COCH[(CH_2)_mCONH_2]NH_2$,
$COCH[(CH_2)_mCONH_2]NHCOOA$, $COCH[(CH_2)_mHet^2]NHCOOA$,
$COCH[(CH_2)_mHet^2]NH_2$,
$COCH[(CH_2)_mNHCOOA]NHCOO(CH_2)_mAr^1$,
$COCH[(CH_2)_mNH_2]NHCOO(CH_2)_mAr^1$,
$COCH(NHCOA)CH_2CONH_2$, $(CH_2)_mNHCOOA$,
$COCH[(CH_2)_mCN]NHCOOA$, $COO(CH_2)_mCN$, $COO(CH_2)_mN(R^6)_2$,
and/or $CO(CH_2)_mCON(R^6)_2$
$NR^6COA$, $NR^6SO_2A$, $COR^6$, $SO_2NR^6$, $S(O)_qA$, NHCONH—$(CH_2)_m$—
Cyc-$OR^6$, $CONH(CH_2)_pOR^6$, $O(CH_2)_pOR^6$, CHO, $(CH_2)_mHet^2$,
$COHet^2$, $(CH_2)_rNH(CH_2)_mHet^2$, $(CH_2)_mNH(CH_2)_mAr^1$,
$NH(CH_2)_pN(R^6)_2$, $(CH_2)_mAr^1$, $O(CH_2)_mAr^1$ and/or =O (carbonyl oxygen),
and in which one N may also be oxidised, Cyc denotes cycloalkylene having 3-7 C atoms, $Ar^1$ denotes phenyl which is unsubstituted or mono-, di-, tri-, tetra- or pentasubstituted by Hal, A, $OR^6$, $COOR^6$, $CON(R^6)_2$, $NR^6COA$, $SO_2NH_2$ and/or $CONH(CH_2)_pHet^2$, $Carb^1$ denotes

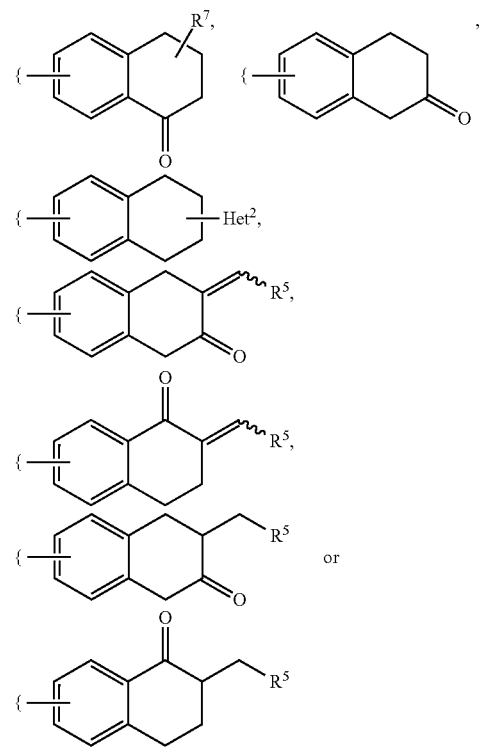

$R^5$ denotes $OR^6$, $COOR^6$, $CON(R^6)_2$ or $Het^1$, $R^7$ denotes $(CH_2)_rCON(R^6)_2$, $(CH_2)_rCON[(CH_2CH_2)OH]_2$ or $(CH_2)_rCONH(CH_2CH_2)OH$, $Het^1$ denotes imidazolyl, pyrazolyl or 4-chloro-2-methylpyrazolyl, $Het^2$ denotes a monocyclic aromatic or saturated heterocycle having 1 to 2 N, and/or O and/or S atoms which is unsubstituted or mono-, di- or trisubstituted by Hal, A, $OR^6$, NHCOA, $N(R^6)_2$ and/or =O (carbonyl oxygen), A denotes unbranched or branched alkyl having 1-10 C atoms, in which 1-7H atoms may be replaced by F, Cl, Br and/or OH, or cyclic alkyl having 3-7 C atoms, Hal denotes F, Cl, Br or I, m denotes 0, 1, 2, 3, 4, 5 or 6, n denotes 1 or 2, p denotes 1, 2, 3 or 4, q denotes 0, 1, 2, 3 or 4, r denotes 0, 1 or 2, and pharmaceutically usable salts, tautomers and stereoisomers thereof, including mixtures thereof in all ratios.

The invention was based on the object of finding novel compounds having valuable properties, in particular those which can be used for the preparation of medicaments.

It has been found that the compounds of the formula I and salts thereof have very valuable pharmacological properties while being well tolerated.

In particular, they exhibit a regulatory, modulatory and/or inhibiting action on metal proteases, preferably on methionine aminopeptidase (MetAP), particularly on the sub-type MetAP-2.

They can be used as medicaments against cancer, but also as medicaments which positively influence fat metabolism, but also as medicaments against inflammation.

Other purine derivatives for combating cancer are disclosed in WO 2007/017069.

WO 01/79157 describes substituted hydrazides and N-alkoxyamides which have MetAP-2 inhibitory activity and can be used for the inhibition of angiogenesis, in particular for the treatment of diseases, such as, for example, cancer, whose development is dependent on angiogenesis.

WO 02/081415 describes MetAP-2 inhibitors which can be used for the treatment of cancer, haemangioma, proliferative retinopathy, rheumatoid arthritis, atherosclerotic neovascularisation, psoriasis, ocular neovascularisation and obesity.

WO 2008/011114 describes compounds as angiogenesis inhibitors and MetAP-2 inhibitors which can be used for the treatment of lymphoid leukaemia and lymphoma.

The action of the compounds according to the invention against cancer lies in particular in their action against angiogenesis. Angiogenesis inhibition has proven helpful in more than 70 diseases, such as, for example, ovarian cancer (F. Spinella et al. J. Cardiovasc. Pharmacol. 2004, 44, S140), breast cancer (A. Morabito et al. J. Cardiovasc. Pharmacol. 2004, 49, 91), prostate cancer (B. Nicholson et al. Cancer Metastas. Rev. 2001, 20, 297), diabetic blindness, psoriasis and macular degeneration (E. Ng et al. Can. J. Ophthalmol. 2005, 23, 3706).

Proteases regulate many different cell processes, particularly the modulation of peptides and proteins, particularly protein conversion, protein ripening and signal peptide processing, the breakdown of abnormal proteins and the deactivation/activation of regulatory proteins. In particular, the amino-terminal modification of nascent polypeptides represents the most frequent modulation. Aminoproteases are metalloproteases which cleave off amino acids from the unprotected N terminus of peptides or proteins, which can be carried out in either a co- or post-translatory manner.

Methionine aminopeptidase (MetAP) cleaves terminal methionine of nascent peptides in particular if the penultimate amino acid is small and uncharged (for example Gly, Ala, Ser, Thr, Val, Pro or Cys).

In many disease processes, angiogenesis is either causally at the centre of the disease or has a worsening effect on the progression of the disease. In cancer events, for example, angiogenesis results in the tumour increasing in size and being able to enter other organs. Other diseases in which angiogenesis plays an important role are psoriasis, arthrosis, arteriosclerosis and eye diseases, such as diabetic retinopathy, age-induced macular degeneration, rubeosis iridis or neovascular glaucoma, furthermore in inflammations.

The compounds of the formula I on which this invention is based, compositions which comprise these compounds, and the processes described can thus be employed for the treatment of these diseases.

Accordingly, the compounds according to the invention or a pharmaceutically acceptable salt thereof are administered for the treatment of cancer, including solid carcinomas, such as, for example, carcinomas (of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an anti-carcinogenic action. The compounds according to the invention are administered to a patient having a disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

It has been found that the compounds according to the invention cause specific inhibition of MetAP-2. The compounds according to the invention preferably exhibit an advantageous biological activity which can be detected in the tests described, for example, herein. In such tests, the compounds according to the invention exhibit and cause an inhibiting effect, which is usually documented by $IC_{50}$ values in a suitable range, preferably in the micromolar range and more preferably in the nanomolar range.

In addition, the compounds according to the invention can be used to achieve additive or synergistic effects in certain existing cancer chemotherapies and radiotherapies and/or to restore the efficacy of certain existing cancer chemotherapies and radiotherapies.

Compounds of the formula I are also taken to mean the hydrates and solvates of these compounds, furthermore pharmaceutically usable derivatives.

The invention also relates to the optically active forms (stereoisomers), salts, the enantiomers, the racemates, the diastereomers and the hydrates and solvates of these compounds. The term solvates of the compounds is taken to mean adductions of inert solvent molecules onto the compounds which form owing to their mutual attractive force. Solvate are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I and pharmaceutically usable salts, tautomers and stereoisomers thereof, characterised in that a compound of the formula II

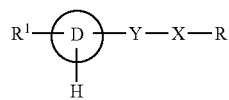

in which $R^1$, X, Y and R have the meanings indicated in Claim 1, is reacted with a compound of the formula III

Z—Cl III in which Z has the meaning indicated in Claim 1, and/or a base or acid of the formula I is converted into one of its salts.

Above and below, the radicals R, X, Y, Z, $R^3$ and $R^4$ have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cycloalkyl preferably denotes cyclopropyl, cyclobutyl, cyclopentyl, cyclohexyl or cycloheptyl.

$R^1$ preferably denotes H, A or COA, very particularly preferably H, methyl oder acetyl.

$R^2$ preferably denotes H or $NH_2$, $R^6$ preferably denotes H, methyl, ethyl, propyl or butyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or pacetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl; furthermore naphthyl or biphenyl.

Ar furthermore preferably denotes phenyl, naphthyl or biphenyl, each of which is unsubstituted or mono-, di-, tri-, tetra- or pentasubstituted by Hal, A, $OR^6$, $N(R^6)_2$, $NO_2$, CN, $COOR^6$, $CON(R^6)_2$, $NR^6COA$, $NR^6SO_2A$, $COR^6$, $SO_2N(R^6)_2$, $S(O)_qA$, $SO_2OH$, $CH=CH—CONH(CH_2)_pOH$, NHCONH-Het, NHCONHA, $(CH_2)_mAr^1$, $O(CH_2)_mAr^1$, $O(CH_2)_mHet^2$, $O(CH_2)_mCOOR^6$,

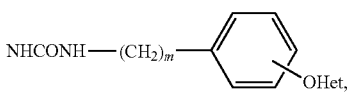

$(CH_2)_m$Het, $CH_2NH[(CH_2)_2O]_q[(CH_2)_2O]_q(CH_2)_pNH_2$, $CH_2N(COA)CH_2CH(OH)CH_2OH$, $CH_2NH(CH_2)_q$Het, $CH_2N(COA)(CH_2)_q$Het, $CH_2N(CHO)(CH_2)_q$Het, COHet, $NHCOCH[(CH_2)_mCOOA]NHCOO(CH_2)_mAr^1$, NHCOCH $[(CH_2)_mCONH_2]NHCOOA$, $NHCOCH[(CH_2)_mCOOH]$ NHCOOH, $NHCOCH[(CH_2)_mHet^2]NHCOOA$, NHCOCH $[(CH_2)_mHet^2]NH_2$, $NHCOCH[(CH_2)_mCONH_2]NH_2$, $CH=CH-COOR^6$ and/or $CH=CH-CON(R^6)_2$.

Ar very particularly preferably denotes phenyl, naphthyl or biphenyl, each of which is unsubstituted or mono-, di-, tri-, tetra- or pentasubstituted by Hal, A, $OR^6$, $N(R^6)_2$, $[C(R^6)_2]_rCN$, $(CH_2)_mCOOR^6$ and/or $CH_2NH(CH_2)_q$Het.

$Ar^1$ preferably denotes phenyl which is unsubstituted or mono-, di- or trisubstituted by Hal and/or $SO_2NH_2$.

X preferably denotes $O(CH_2)_r$, NH, NA, OC(=O), $NHSO_2$ or is absent.

Y preferably denotes $(CH_2)_n$ or it is absent.

R preferably denotes H, Ar or Het.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Unsubstituted Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het furthermore preferably denotes a mono- or bicyclic saturated, unsaturated or aromatic heterocycle having 1 to 4 N, and/or O and/or S atoms which is un-substituted or mono-, di- or trisubstituted by Hal, A, $(CH_2)_mOR^6$, $(CH_2)_mN(R^6)_2$, $(CH_2)_mCN$, $(CH_2)_mCOOR^6$, $CONH(CH_2)_mCOOH$, $CONH(CH_2)_mHet^2$, $CO(CH_2)_mN(R^6)_2$, $CO(CH_2)_mNH(CH_2)_rCOOA$, $(CH_2)_rCONH(CH_2)_mAr^1$, $COCH[(CH_2)_mCONH_2]NH_2$, $COCH[(CH_2)_mCONH_2]NHCOOA$, $COCH[(CH_2)_mHet^2]NHCOOA$, $COCH(NHCOA)CH_2CONH_2$, $(CH_2)_mNHCOOA$, $COCH[(CH_2)_mCN]NHCOOA$, $COO(CH_2)_mCN$, $COO(CH_2)_mN(R^6)_2$, $CO(CH_2)_mCON(R^6)_2$, $COR^6$, $COHet^2$, $O(CH_2)_mAr^1$ and/or =O (carbonyl oxygen), Het particularly preferably denotes pyridazinyl, pyrazolyl, benzimidazolyl, pyridyl, dibenzofuranyl, carbazolyl, indolyl, dihydroindolyl, benzofuranyl, dihydrobenzofuranyl, piperazinyl, morpholinyl, quinolinyl, isoquinolinyl, isoindolyl, dihydroquinolinyl, dihydroisoquinolinyl, tetrahydroquinolinyl, tetrahydroisoquinolinyl, quinazolinyl, quinoxalinyl, phthalazinyl, purinyl, naphthyridinyl, pyrimidinyl, indazolyl, furyl, thienyl, imidazolyl, pyrrolyl, oxazolyl, isoxazolyl, thiazolyl, triazolyl, tetrazolyl, thiadiazole, benzothiazolyl, imidazo[1,2-a]-pyridinyl, 1,3-benzodioxolyl or benzoxazolyl, each of which is unsubstituted or mono-, di- or trisubstituted by Hal, A, $(CH_2)_mOR^6$, $(CH_2)_mN(R^6)_2$, $(CH_2)_mCN$, $(CH_2)_mCOOR^6$, $CONH(CH_2)_mCOOH$, $CONH(CH_2)_mHet^2$, $CO(CH_2)_mN(R^6)_2$, $CO(CH_2)_mNH(CH_2)_rCOOA$, $(CH_2)_rCONH(CH_2)_mAr^1$, $COCH[(CH_2)_mCONH_2]NH_2$, $COCH[(CH_2)_mCONH_2]NHCOOA$, $COCH[(CH_2)_mHet^2]NHCOOA$, $COCH(NHCOA)CH_2CONH_2$, $(CH_2)_mNHCOOA$, $COCH[(CH_2)_mCN]NHCOOA$, $COO(CH_2)_mCN$, $COO(CH_2)_mN(R^6)_2$, $CO(CH_2)_mCON(R^6)_2$, $COR^6$, $COHet^2$, $O(CH_2)_mAr^1$ and/or =O.

Het furthermore preferably denotes a quinolinyl, isoquinolinyl, pyrazolyl or isoindolyl, each of which is mono-, di- or trisubstituted by Hal, A, $(CH_2)_mOR^6$, $(CH_2)_mN(R^6)_2$, $(CH_2)_mCN$, $(CH_2)_mCOOR^6$, $CONH(CH_2)_mCOOH$, $CONH(CH_2)_mHet^2$, $CO(CH_2)_mN(R^6)_2$, $CO(CH_2)_mNH(CH_2)_rCOOA$, $(CH_2)_rCONH(CH_2)_mAr^1$, $COCH[(CH_2)_mCONH_2]NH_2$, $COCH[(CH_2)_mCONH_2]NHCOOA$, $COCH[(CH_2)_mHet^2]NHCOOA$, $COCH(NHCOA)CH_2CONH_2$, $(CH_2)_mNHCOOA$, $COCH[(CH_2)_mCN]NHCOOA$, $COO(CH_2)_mCN$, $COO(CH_2)_mN(R^6)_2$, $CO(CH_2)_mCON(R^6)_2$, $COR^6$, $COHet^2$, $O(CH_2)_mAr^1$ and/or =O.

Cyc preferably denotes cyclobutylene, cyclopentylene or cyclohexylene.

$Het^2$ preferably denotes furyl, thienyl, pyrrolyl, oxazolyl, isoxazolyl, thiazolyl, imidazolyl, pyridyl, pyrimidinyl, piperazinyl, morpholinyl, piperidinyl, pyrrolidinyl, azetidinyl, dihydrofuranyl or tetrahydrofuranyl, each of which is unsubstituted or mono- or disubstituted by A, $OR^6$, NHCOA and/or =O (carbonyl oxygen).

$Het^2$ particularly preferably denotes imidazolyl, indolyl, isoxazolyl, pyridazinyl, pyrazolyl, benzimidazolyl, pyridyl, dibenzofuranyl, carbazolyl, benzofuranyl, isoindolyl, quinazolinyl, quinoxalinyl, pyrimidinyl, indazolyl, furyl, thienyl, pyrrolyl, oxazolyl, thiazolyl, triazolyl, tetrazolyl, thiadiazole, benzothiazolyl, imidazo-[1,2-a]pyridinyl or 1,3-benzodioxolyl.

Hal preferably denotes F, Cl or Br, but also I, particularly preferably F or Cl.

The invention preferably relates to the compounds of the formula I which are indicated by the following sub-formulae Ia to Ik

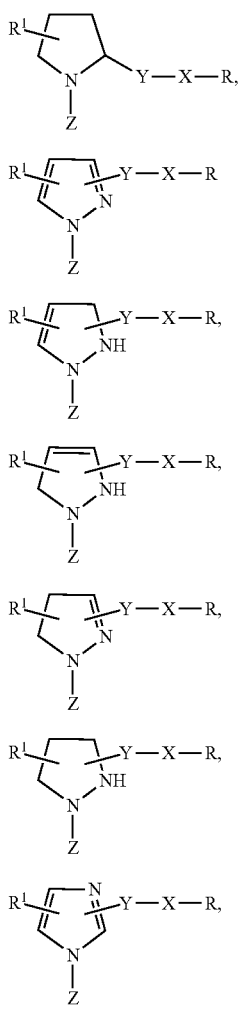
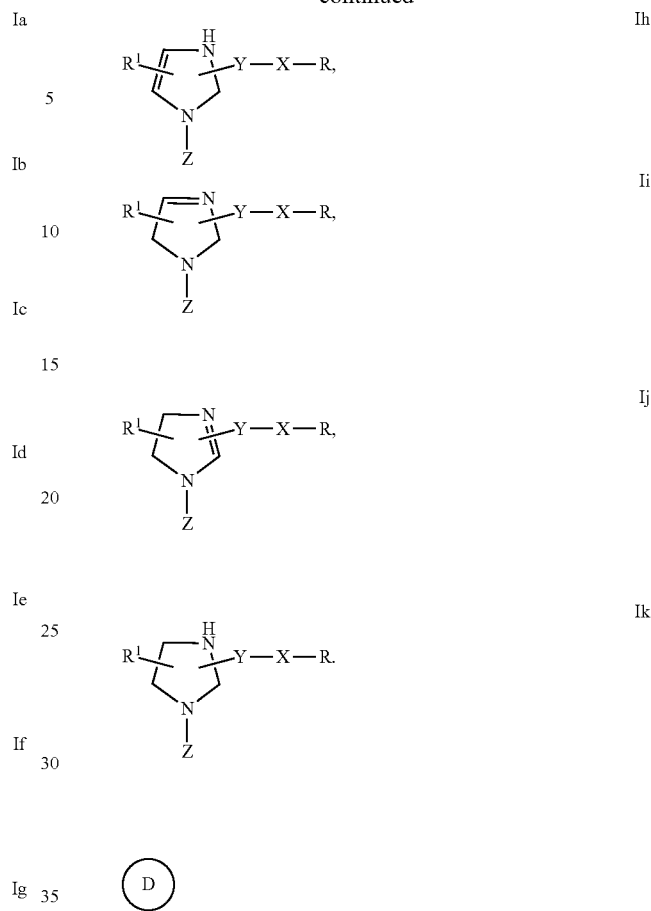
preferably denotes pyrrolidinyl, imidazolinyl, pyrazolyl, 2-oxa-5-azabicyclo[2.2.1]hept-5-yl, morpholinyl or N, very particularly preferably pyrrolidinyl.
Z preferably denotes
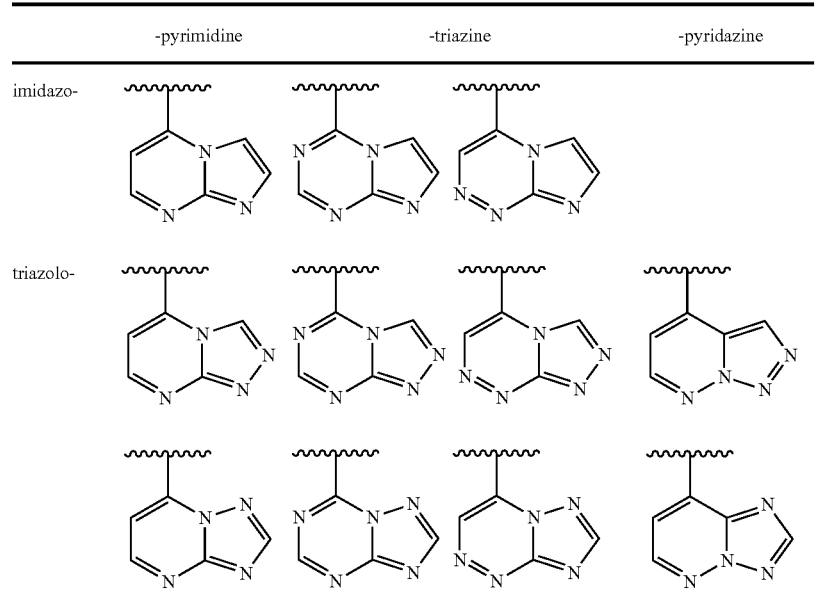

|  | -pyrimidine | -triazine | -pyridazine |
|---|---|---|---|
| tetrazolo- | | | |
| pyrazolo- | | | |

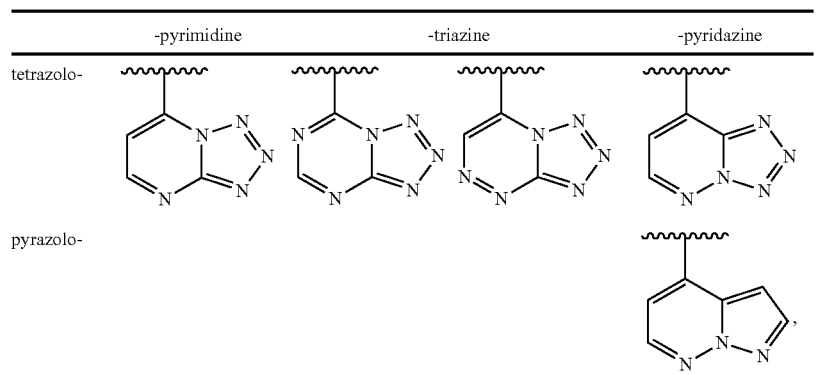

and pyrrolopyrimidinyl, where the said radicals may be substituted by $R^2$.

Z particularly preferably denotes imidazopyrimidinyl, triazolopyrimidinyl or pyrrolopyrimidinyl,
where Z is bonded to a nitrogen of the radical D.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Iaa to Inn, which conform to the formula I and in which the radicals not designated in greater detail have the meaning indicated for the formula I, but in which in Iaa

denotes pyrrolidinyl, imidazolinyl, pyrazolyl, 2-oxa-5-azabicyclo[2.2.1]hept-5-yl, morpholinyl or N;
in Ibb Z denotes imidazopyrimidinyl, triazolopyrimidinyl or pyrrolopyrimidinyl,
where Z is bonded to a nitrogen of the radical D;
in Icc R denotes H, Ar or Het;
in Idd Ar denotes phenyl, naphthyl or biphenyl, each of which is unsubstituted or mono-, di-, tri-, tetra- or pentasubstituted by Hal, A, $OR^6$, $N(R^6)_2$, $[C(R^6)_2]_rCN$, $(CH_2)_mCOOR^6$ and/or $CH_2NH(CH_2)_qHet$;
in Iee Het denotes a mono- or bicyclic saturated, unsaturated or aromatic heterocycle having 1 to 4 N, and/or O and/or S atoms which is unsubstituted or mono-, di- or trisubstituted by Hal,
A, $(CH_2)_mOR^6$, $(CH_2)_mN(R^6)_2$, $(CH_2)_mCN$, $(CH_2)_mCOOR^6$,
$CONH(CH_2)_mCOOH$, $CONH(CH_2)_mHet^2$, $CO(CH_2)_mN(R^6)_2$,
$CO(CH_2)_mNH(CH_2)_rCOOA$, $(CH_2)_rCONH(CH_2)_mAr^1$,
$COCH[(CH_2)_mCONH_2]NH_2$,
$COCH[(CH_2)_mCONH_2]NHCOOA$,
$COCH[(CH_2)_mHet^2]NHCOOA$,
$COCH(NHCOA)CH_2CONH_2$, $(CH_2)_mNHCOOA$,
$COCH[(CH_2)_mCN]NHCOOA$, $COO(CH_2)_mCN$,
$COO(CH_2)_mN(R^6)_2$, $CO(CH_2)_mCON(R^6)_2$, $COR^6$, $COHet^2$,
$O(CH_2)_mAr^1$ and/or =O (carbonyl oxygen);
in Iff $Ar^1$ denotes phenyl which is unsubstituted or mono-, di- or trisubstituted by Hal and/or $SO_2NH_2$;
in Igg Het denotes pyridazinyl, pyrazolyl, benzimidazolyl, pyridyl, dibenzofuranyl, carbazolyl, indolyl, dihydroindolyl, benzofuranyl, dihydrobenzofuranyl, piperazinyl, morpholinyl, quinolinyl, isoquinolinyl, isoindolyl, dihydroquinolinyl, dihydroisoquinolinyl, tetrahydroquinolinyl, tetrahydroisoquinolinyl, quinazolinyl, quinoxalinyl, phthalazinyl, purinyl, naphthyridinyl, pyrimidinyl, indazolyl, furyl, thienyl, imidazolyl, pyrrolyl, oxazolyl, isoxazolyl, thiazolyl, triazolyl, tetrazolyl, thiadiazole, benzothiazolyl, imidazo[1,2-a]pyridinyl, 1,3-benzodioxolyl or benzoxazolyl, each of which is unsubstituted or mono-, di- or trisubstituted by Hal, A, $(CH_2)_mOR^6$,
$(CH_2)_mN(R^6)_2$, $(CH_2)_mCN$, $(CH_2)_mCOOR^6$,
$CONH(CH_2)_mCOOH$, $CONH(CH_2)_mHet^2$, $CO(CH_2)_mN(R^6)_2$,
$CO(CH_2)_mNH(CH_2)_rCOOA$, $(CH_2)_rCONH(CH_2)_mAr^1$,
$COCH[(CH_2)_mCONH_2]NH_2$,
$COCH[(CH_2)_mCONH_2]NHCOOA$,
$COCH[(CH_2)_mHet^2]NHCOOA$,
$COCH(NHCOA)CH_2CONH_2$, $(CH_2)_mNHCOOA$,
$COCH[(CH_2)_mCN]NHCOOA$, $COO(CH_2)_mCN$,
$COO(CH_2)_mN(R^6)_2$, $CO(CH_2)_mCON(R^6)_2$, $COR^6$, $COHet^2$,
$O(CH_2)_mAr^1$ and/or =O;
In Ihh Het denotes quinolinyl, isoquinolinyl, pyrazolyl or isoindolyl, each of which is mono-, di- or trisubstituted by Hal, A,
$(CH_2)_mOR^6$, $(CH_2)_mN(R^6)_2$, $(CH_2)_mCN$, $(CH_2)_mCOOR^6$,
$CONH(CH_2)_mCOOH$, $CONH(CH_2)_mHet^2$, $CO(CH_2)_mN(R^6)_2$,
$CO(CH_2)_mNH(CH_2)_rCOOA$, $(CH_2)_rCONH(CH_2)_mAr^1$,
$COCH[(CH_2)_mCONH_2]NH_2$,
$COCH[(CH_2)_mCONH_2]NHCOOA$,
$COCH[(CH_2)_mHet^2]NHCOOA$,
$COCH(NHCOA)CH_2CONH_2$, $(CH_2)_mNHCOOA$,
$COCH[(CH_2)_mCN]NHCOOA$, $COO(CH_2)_mCN$,
$COO(CH_2)_mN(R^6)_2$, $CO(CH_2)_mCON(R^6)_2$, $COR^6$, $COHet^2$,
$O(CH_2)_mAr^1$ and/or =O;
in Iii A denotes unbranched or branched alkyl having 1-6 C atoms, in which 1-5H atoms may be replaced by F and/or Cl;
in Ijj $R^1$ denotes H, A or COA;

in Ikk $R^2$ denotes H or $NH_2$;
in Ill Y denotes $(CH_2)_n$ or is absent;
in Imm X denotes $O(CH_2)_r$, NH, NA, OC(=O), $NHSO_2$ or is absent;
in Inn (D)

denotes pyrrolidinyl, imidazolinyl, pyrazolyl, 2-oxa-5-azabicyclo[2.2.1]hept-5-yl, morpholinyl or N, Z denotes imidazopyrimidinyl, triazolopyrimidinyl or pyrrolopyrimidinyl,
  where Z is bonded to a nitrogen of the radical D,
Y denotes $(CH_2)_n$ or is absent,
X denotes $O(CH_2)_r$, NH, NA, OC(=O), $NHSO_2$ or is absent,
$R^1$ denotes H, A or COA,
$R^2$ denotes H or $NH_2$,
R denotes H, Ar or Het,
Ar denotes phenyl, naphthyl or biphenyl, each of which is unsubstituted or mono-, di-, tri-, tetra- or pentasubstituted by Hal, A, $OR^6$, $N(R^6)_2$, $[C(R^6)_2]_rCN$, $(CH_2)_mCOOR^6$ and/or $CH_2NH(CH_2)_q$Het,
Het denotes a mono- or bicyclic saturated, unsaturated or aromatic heterocycle having 1 to 4 N, and/or O and/or S atoms which is unsubstituted or mono-, di- or trisubstituted by Hal,
  A, $(CH_2)_mOR^6$, $(CH_2)_mN(R^6)_2$, $(CH_2)_mCN$, $(CH_2)_mCOOR^6$,
  $CONH(CH_2)_mCOOH$, $CONH(CH_2)_mHet^2$, $CO(CH_2)_mN(R^6)_2$,
  $CO(CH_2)_mNH(CH_2)_rCOOA$, $(CH_2)_rCONH(CH_2)_mAr^1$,
  $COCH[(CH_2)_mCONH_2]NH_2$,
  $COCH[(CH_2)_mCONH_2]NHCOOA$,
  $COCH[(CH_2)_mHet^2]NHCOOA$,
  $COCH(NHCOA)CH_2CONH_2$, $(CH_2)_mNHCOOA$,
  $COCH[(CH_2)_mCN]NHCOOA$, $COO(CH_2)_mCN$,
  $COO(CH_2)_mN(R^6)_2$, $CO(CH_2)_mCON(R^6)_2$, $COR^6$, $COHet^2$,
  $O(CH_2)_mAr^1$ and/or =O (carbonyl oxygen),
$Het^2$ denotes imidazolyl, indolyl, isoxazolyl, pyridazinyl, pyrazolyl, benzimidazolyl, pyridyl, dibenzofuranyl, carbazolyl, benzofuranyl, isoindolyl, quinazolinyl, quinoxalinyl, pyrimidinyl, indazolyl, furyl, thienyl, pyrrolyl, oxazolyl, thiazolyl, triazolyl, tetrazolyl, thiadiazole, benzothiazolyl, imidazo[1,2-a]-pyridinyl or 1,3-benzodioxolyl,
$R^6$ denotes H or alkyl having 1-6 C atoms,
$Ar^1$ denotes phenyl which is unsubstituted or mono-, di- or trisubstituted by Hal and/or $SO_2NH_2$,
Hal denotes F, Cl, Br or I,
m denotes 0, 1, 2, 3, 4, 5 or 6,
n denotes 1 or 2,
q denotes 0, 1, 2, 3 or 4,
r denotes 0, 1 or 2;
and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting compounds of the formula II with a compound of the formula III.

The compounds of the formula II and of the formula III are generally known. If they are novel, however, they can be prepared by methods known per se.

The reaction is carried out in an inert solvent and is generally carried out in the presence of an acid-binding agent, preferably an organic base, such as DIPEA, triethylamine, dimethylaniline, pyridine or quinoline.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

Depending on the conditions used, the reaction time is between a few minutes and 14 days, the reaction temperature is between about −15° and 150°, normally between 40° and 130°, particularly preferably between 60° and 110° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to glycol ethers, such as ethylene glycol monomethyl ether, THF, dichloromethane and/or DMF.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$) alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$) alkyl halides, for example decyl, dodecyl, lauryl, myristyl and stearyl chloride, bromide and iodide; and aryl($C_1$-$C_4$) alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal anti-bodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable salts and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable salts and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable salts and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment and control of diseases.

These diseases include the proliferation of tumour cells, pathological neovascularisation (or angiogenesis), which promotes the growth of solid tumours, neovascularisation in the eye (diabetic retinopathy, age-induced macular degeneration and the like) and inflammation (psoriasis, rheumatoid arthritis and the like), and proliferative diseases of the mesangial cells.

The present invention encompasses the use of the compounds of the formula I and/or physiologically acceptable salts and solvates thereof for the preparation of a medicament for the treatment or prevention of tumours, tumour diseases and/or tumour metastases.

The tumour disease is preferably selected from the group tumour of the squamous epiofthelium, of the bladder, of the stomach, of the kidneys, of head and neck, of the oesophagus, of the cervix, of the thyroid, of the intestine, of the liver, of the brain, of the prostate, of the urogenital tract, of the lymphatic system, of the stomach, of the larynx, of the lung, of the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma.

Likewise encompassed is the use of the compounds according to Claim 1 according to the invention and/or physiologically acceptable salts and solvates thereof for the preparation of a medicament for the treatment of osteoporosis, diabetes and obesity.

Likewise encompassed is the use of the compounds according to Claim 1 according to the invention and/or physiologically acceptable salts and solvates thereof for the preparation of a medicament for the treatment or prevention of a disease in which angiogenesis is involved.

A disease of this type in which angiogenesis is involved is an eye disease, such as retina vascularisation, diabetic retinopathy, age-induced macular degeneration and the like.

The angiogenic disease is preferably selected from the group diabetic retinopathy, arthritis, cancer, psoriasis, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome.

The proliferative disease of the mesangial cells is preferably selected from the group
glomerulonephritis, diabetic nephropathy, malignant nephrosclerosis, thrombotic microangiopathy syndrome, transplant rejection, glomerulopathy.

The use of compounds of the formula I and/or physiologically acceptable salts and solvates thereof for the preparation of a medicament for the treatment or prevention of inflammatory diseases likewise falls within the scope of the present invention. Examples of such inflammatory diseases include rheumatoid arthritis, psoriasis, contact dermatitis, delayed hypersensitivity reaction and the like.

The inflammatory disease is preferably selected from the group Inflammatory bowel disease, arthritis, atherosclersosis, asthma, allergies, inflammatory kidney diseases, multiple sclerosis, chronic obstructive pulmonary disease, inflammatory skin diseases, pardontal diseases, psoriasis, T-cell-promoted immune disease.

The inflammatory bowel disease is preferably selected from the group ulcerative colitis, Crohn's disease, non-specific colitis.

The T-cell-promoted immune disease is preferably selected from the group allergic encephalomyelitis, allergic neuritis, transplant rejection, graft-versus-host reaction, myocarditis, thyroiditis, nephritis, systemic lupus erythematosus, insulin-dependent diabetes mellitus.

The arthritis disease is preferably selected from the group rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome.

The inflammatory kidney disease is preferably selected from the group glomerulonephritis, glomerular injury, nephrotic syndrome, interstitial nephritis, lupus nephritis, Goodpasture's syndrome, Wegener's granulomatosis, renal vasculitis, IgA nephropathy, idiopatic glomerular disease.

The inflammatory skin disease is preferably selected from the group psoriasis, atopic dermatitis, contact sensitivity, acne.

Likewise encompassed is the use of the compounds of the formula I and/or physiologically acceptable salts and solvates thereof for the preparation of a medicament for the treatment or prevention of a disease or condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Likewise encompassed is the use of the compounds of the formula I and/or physiologically acceptable salts thereof for the preparation of a medicament for the treatment and/or combating of a tumour-induced disease in a mammal, in which to this method a therapeutically effective amount of a compound according to the invention is administered to a sick mammal in need of such treatment. The therapeutic amount varies according to the specific disease and can be determined by the person skilled in the art without undue effort.

The disclosed compounds of the formula I can be administered in combination with other therapeutic agents, including anticancer agents. As used here, the term "anticancer agent" relates to any agent which is administered to a patient with cancer for the purposes of treating the cancer.

The compounds of the formula I may also be administered together with other well-known therapeutic agents that are selected for their particular suitability for the condition being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)-ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide. "Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamineplatinum(II)]bis-[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-Nmethyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]-pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo-[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]-quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Evidence of the Action of Pharmacological Inhibitors on the Proliferation/Vitality of Tumour Cells in vitro 1.0 Background In the present experiment description, the inhibition of tumour cell proliferation/tumour cell vitality by active ingredients is described.

The cells are sown in a suitable cell density in microtitre plates (96-well format) and the test substances are added in the form of a concentration series. After four further days of cultivation in serum-containing medium, the tumour cell proliferation/tumour cell vitality can be determined by means of an Alamar Blue test system.

2.0 Experimental Procedure 2.1 Cell Culture

For example commercially available colon carcinoma cell lines, ovary cell lines, prostate cell lines or breast cell lines, etc.

The cells are cultivated in medium. At intervals of several days, the cells are detached from the culture dishes with the aid of trypsin solution and sown in suitable dilution in fresh medium. The cells are cultivated at 37° Celsius and 10% $CO_2$.

2.2. Sowing of the Cells

A defined number of cells (for example 2000 cells) per culture/well in a volume of 180 µl of culture medium are sown in microtitre plates (96 well cell-culture plates) using a multichannel pipette. The cells are subsequently cultivated in a CO2 incubator (37° C. and 10% CO2).

2.3. Addition of the Test Substances

The test substances are dissolved, for example, in DMSO and subsequently employed in corresponding concentration (if desired in a dilution series) in the cell culture medium. The dilution steps can be adapted depending on the efficiency of the active ingredients and the desired spread of the concentrations. Cell culture medium is added to the test substances in corresponding concentrations. The addition of the test substances to the cells can take place on the same day as the sowing of the cells. To this end, in each case 20 µl of substance solution from the predilution plate are added to the cultures/wells. The cells are cultivated for a further 4 days at 37° Celsius and 10% $CO_2$.

2.4. Measurement of the Colour Reaction

In each case, 20 µl of Alamar Blue reagent are added per well, and the microtitre plates are incubated, for example, for a further seven hours in a $CO_2$ incubator (at 37° C. and 10% CO2). The plates are measured in a reader with a fluorescence filter at a wavelength of 540 nm. The plates can be shaken gently immediately before the measurement.

3. Evaluation

The absorbance value of the medium control (no cells and test substances used) is subtracted from all other absorbance values. The controls (cells without test substance) are set equal to 100 percent, and all other absorbance values are set in relation thereto (for example in % of control):

Calculation:

$$\frac{100 * \left( \begin{array}{c} \text{value with cells and test substance} - \\ \text{value of medium control} \end{array} \right)}{(\text{value with cells} - \text{value of medium control})}$$

$IC_{50}$ values (50% inhibition) are determined with the aid of statistics programs, such as, for example, RS1.

$IC_{50}$ data for compounds according to the invention are shown in Table 1.

| Material | Order No. | Manufacturer |
|---|---|---|
| Microtitre plates for cell culture (Nunclon Surface 96-well plate) | 167008 | Nunc |
| DMEM | P04-03550 | Pan Biotech |
| PBS (10x) Dulbecco | 14200-067 | Gibco |
| 96-well plates (polypropylene) | 267334 | Nunc |
| AlamarBlue $^{TM}$ | BUF012B | Serotec |
| FCS | 1302 | Pan Biotech GmbH |
| Trypsin/EDTA solution 10x | L 2153 | Biochrom AG |
| 75 $cm^2$ culture bottles | 353136 | BDFalcon |
| A2780 | 93112519 | ECACC |
| Colo205 | CCL222 | ATCC |

| Material | Order No. | Manufacturer |
| --- | --- | --- |
| MCF7 | HTB22 | ATCC |
| PC3 | CRL-1435 | ATCC |

Determination of the Proliferation Inhibition by Inhibitors of Methionine Aminopeptidase 2 in the BrdU Proliferation Test (Cellular Assay)

The inhibition of proliferation is determined by incorporation of bromodesoxyuridine (BrdU) into human umbilical vein endothelial cells (HUVECs, Promo-Cell, C-12200). The HUVECs are cultivated at 37° C. and 5% CO2 in basal medium (PromoCell, C-22200) with supplement mix (PromoCell, C-39225). After detachment of the cells by means of trypsin/EDTA, the number of living cells is determined, and the cells are sown in a density of 1000 cells per cavity in a total volume of 175 µl (cavities are coated in advance either with supplemented culture medium for 1-2 hours at 37° C. or with 1.5% gelatine for 0.5-2 hours at 37° C.). After cultivation for 24 hours, the test substances are added in various concentrations (for example final concentrations 30 µM to 0.03 nM in 10-fold dilution steps) and a volume of 25 µl. The DMSO concentration is kept constant at 0.3%. After cultivation for a total of 48 or 72 hours, 20 µl of bromodesoxyuridine (Roche, # 11647229001 diluted 1:1000 in culture medium, final concentration 10 µM) are added, and cultivation is continued for a further 20 to 24 hours. After incubation with test substances for a total of 72 or 96 hours, the culture medium is removed, and an immunohistochemical determination is carried out for detection of BrdU incorporation (BrdU ELISA, Roche, # 11647229001). To this end, the cells are treated with a fixative for 30 min at room temperature and subsequently incubated with a peroxidase-labelled anti-BrdU antibody (diluted 1:100 in antibody dilution buffer) for 60 min at room temperature. After washing three times with 1-fold-concentrated DPBS buffer (Gibco, # 14200), the enzymatic reaction is initiated in TMB substrate solution. The colour development is stopped after 15 min by addition of 25 µl of a 1M sulfuric acid solution. A determination of the optical density is carried out within 5 min by measurement at a wavelength of 450 nM. The controls used are cavities containing DMSO-treated cells (100% control) or empty cavities (blank value). The sensitivity of this test to inhibitors of methionine aminopeptidase is checked and confirmed using the inhibitor fumagillin.

MetAP-2 Activity Measurement

The MetAP-2 activity is determined by coupling enzymatic reactions. The tripeptide Met-Arg-Ser (MAS) is employed as substrate. The methionine liberated is firstly converted into $Met_{ox}$ and $H_2O_2$ by L-aminooxidase (AAO). In the second step, the peroxidase (POD) with the aid of the $H_2O_2$ catalyses the oxidation of the leukodye dianisidine to $dianisidine_{ox}$, the increase of which is detected photometrically at 450 nm.

MetAP-2 activity can be recorded continuously as kinetics. The reaction scheme illustrates that one mol of $dianisidine_{ox}$ is formed per mol of methionene. The MetAP-2 enzyme activity can therefore be calculated directly as Δ absorption per time unit. Qualification of the MetAP-2 activity (mol of Met/time unit) is possible with the aid of the $dianisidine_{ox}$ extinction coefficient. The change in extinction per time unit is depicted graphically and a slope calculation is carried out in the visually linear region of the reaction. The activities of the compounds are summarised in Table 1.

Solubility Measurement

Determination by Shake Flask Solubility Measurement

Eluent Preparation:

Eluent A: 2 ml of diethylamine, for synthesis+1000 ml of methanol, LiChrosolv

Eluent B: 5 g of ammonium acetate, for analysis+5 ml of methanol, LiChrosolv+995 ml of ultrapure water Sample Solvent:

Buffer: 3.954 g of sodium dihydrogenphosphate monohydrate+6.024 g of sodium chloride+950 ml of ultrapure water the pH is adjusted using 0.1 M NaOH or 0.1 M HCl.

Sample Preparation:

The samples are shaken at 37° C. and 450 rpm for 24 h.

After about 7 h, the pH of the samples is checked and adjusted if necessary. It is also checked whether the sample is still present in excess.

Just before the end of the 24 h shaking time, the samples are again checked for pH and a precipitate.

Ultrapure water unit: MilliQ gradient, Millipore, instrument: F3PN37462D

Shaker: TiMix control, Bühler

Incubation hood: TH 15 Bühler pH meter: 766 Calimatic Knick instrument: pH 1 pH electrode: InLab 423 Mettler

APCI-MS (atmospheric pressure chemical ionisation-mass spectrometry) $(M+H)^+$.

The substances are generally characterised by HPLC-MS. The column used and the gradient is indicated here. The reported retention time relates to the MS spur (retention in the UV or ELSD spur may differ in the third decimal place).

HPLC: Column: Chromolite Performance RP18-e 50-4.6 mm

Gradient: $ACN/H_2O$ comprising 0.04/0.05% of formic acid

Method: polar Chromolith/Chromolith (extended)

Flow rate: 2.4 ml/min

[M+1-1]

$Agilent Apparatus

Chromolite Performance RP18-e 50-4.6 mm

Gradient: ACN/H2O comprising 0.04/0.05% of formic acid

Method: polar

Flow rate: 2.4 ml/min

The NMR spectra are recorded in $DMSO-d_6$ and in $DMSO-d_6+TFA-d_1$. The data indicated relate to the $DMSO-d_6$ spectra.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

M.p.: melting point

Mass spectrometry (MS): EI (electron impact ionisation) $M^+$

FAB (fast atom bombardment) $(M+H)^+$

ESI (electrospray ionisation) $(M+H)^+$

APCI-MS (Atmospheric Pressure Chemical Ionisation-mass Spectrometry) (M+H)+.
Synthesis schemes for the preparation of some compounds according to the invention:
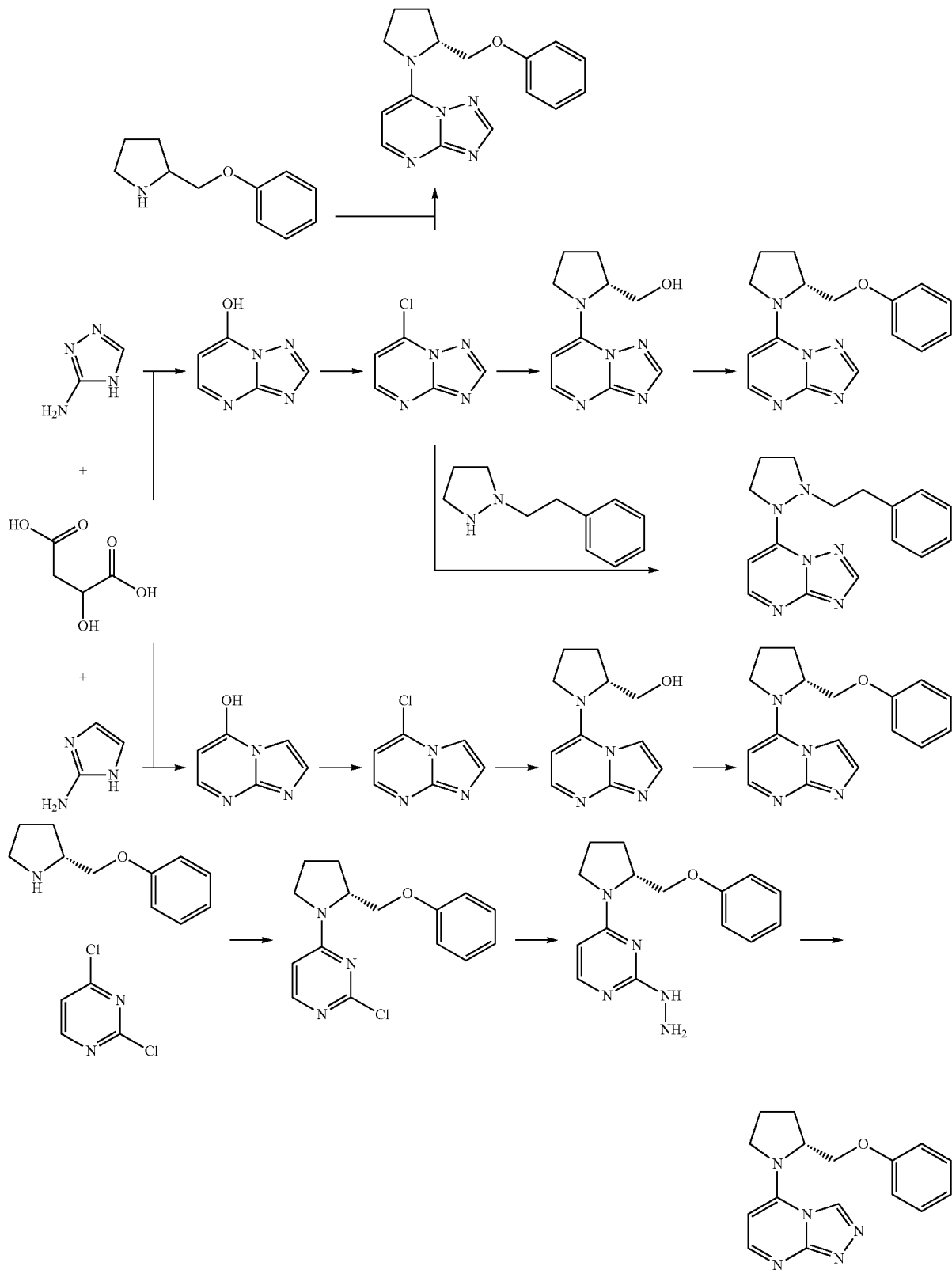

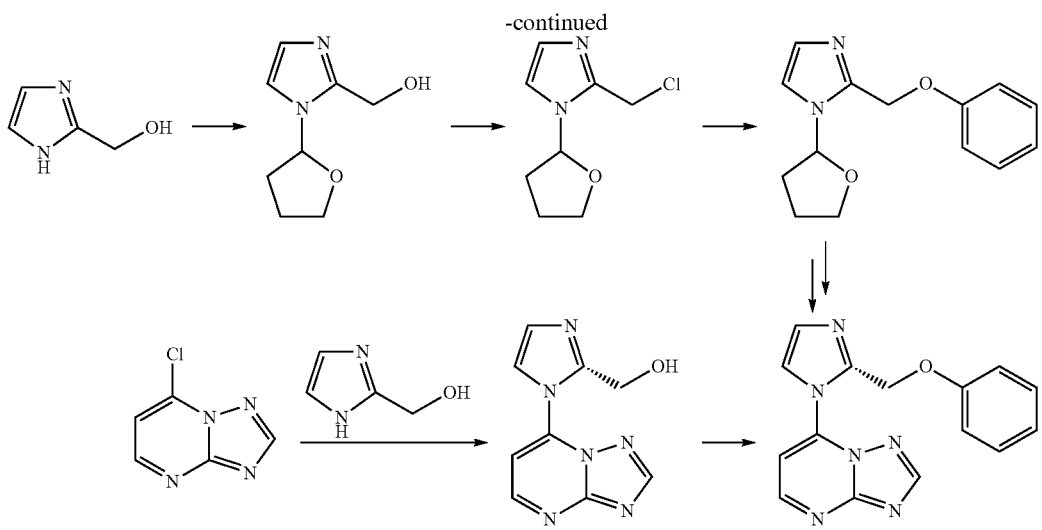

EXAMPLE 1

The preparation of 7-[(R)-2-(naphthalen-1-yloxymethyl) pyrrolidin-1-yl]-[1,2,4]-triazolo[1,5-a]pyrimidine ("A1") is carried out analogously to the following scheme

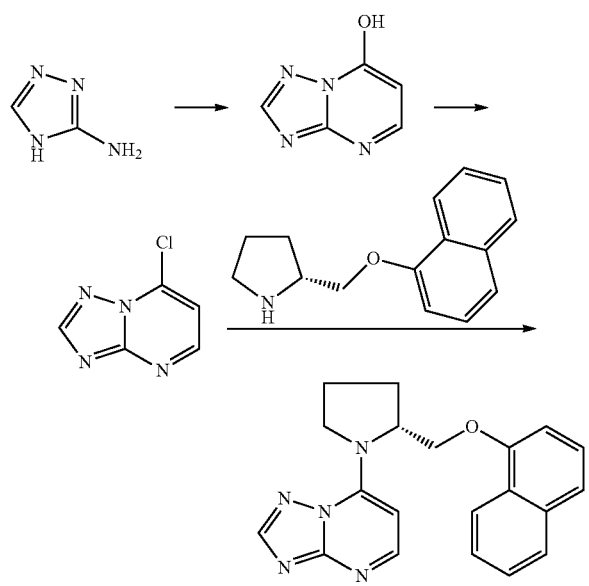

250 ml of conc. sulfuric acid are cooled to 0° C., and 90 g of racemic malic acid are added at such a rate that the temperature does not exceed 10° C. 54 g of 3-amino-[1,2,4]triazole are subsequently introduced in an analogous manner. After 12 h at RT, the suspension is warmed at 100° C. for one hour, giving a clear solution.

For work-up, the reaction solution is allowed to cool to RT, and the batch is poured into 300 ml of ice-water. A pH of 6 is set using concentrated NaOH solution. The crystals which deposit in the process are filtered off with suction, washed with water and dried to constant weight in vacuo at 100° C. The product [1,2,4]triazolo[1,5-a]pyrimidin-7-ol obtained melts at 290° C.; HPLC: 0.475 min; MS: [273.1] (Yasuo Makisumi, Hideo Kano Bull Soc. Chem. Japan 1959, 8, 907; m.p. 286-287° C.).

5.4 g of [1,2,4]triazolo[1,5-a]pyrimidin-7-ol from the first synthesis step are introduced into 20 ml of phosphorus oxychloride with vigorous stirring. After completion, the mixture is warmed under reflux for a further 1.5 h. For work-up, the cooled batch is stirred in portions into 100 ml of ice-water and subsequently adjusted to pH 12 using conc. NaOH solution. The aqueous phase is extracted with ethyl acetate. The combined organic phases are dried over sodium sulfate, and the solvent is removed in vacuo. The 7-chloro-[1,2,4]triazolo[1,5-a]pyrimidine obtained is employed in the following reaction without further purification; m.p. 190° [lit. 186-187° C.]; HPLC: 0.920 min; MS: [157.0].

400 mg of (R)-2-(naphthalen-1-yloxymethyl)pyrrolidine, 500 mg of the 7-chloro-[1,2,4]triazolo[1,5-a]pyrimidine prepared above and 650 mg of N-ethyldiisopropylamine are heated at 130° C. in a microwave for 3 h in 40 ml of 1-butanol. The butanol is subsequently removed in vacuo, the residue is taken up in ethyl acetate, mixed with water, adjusted to pH 12 using 1 N NaOH solution, phases are separated, the organic phase is dried over sodium sulfate, evaporated and chromatographed on silica gel, giving 640 mg of "A1"; m.p. 74-75°;
HPLC: 2.386 min; MS: [346.1];
$^1$H NMR (500 MHz, d$_6$-DMSO) δ [ppm] 8.43 (s, 1H), 8.31 (d, 1H, J=5.7 Hz), 7.83 (d, 1H, J=8.1 Hz), 7.71 (d, 1H, J=8.1 Hz), 7.49 (ddd, 1H, J=1.3 Hz, J=6.9 Hz, J=8.1 Hz), 7.44 (d, 1H, J=8.2 Hz), 7.40 (ddd, 1H, J=1.3 Hz, J=6.9 Hz, J=8.1 Hz), 7.35 (t, 1H, J=7.9 Hz), 6.9 (d, 1H, J=7.7 Hz), 6.43 (d, 1H, J=5.7 Hz), 5.74 (br. m, 1H), 4.39 (dd, 1H, J=5.2 Hz, J=9.7 Hz), 4.20 (dd, 1H, J=6.5 Hz, J=9.7 Hz), 4.00 (br. m, 1H), 3.80 (br. m, 1H), 2.33-2.22 (m, 3H), 2.10 (m, 1H).

EXAMPLE 2

The preparation of 7-pyrazol-1-yl-[1,2,4]triazolo[1,5-a]pyrimidine ("A2") is carried out analogously to the following scheme

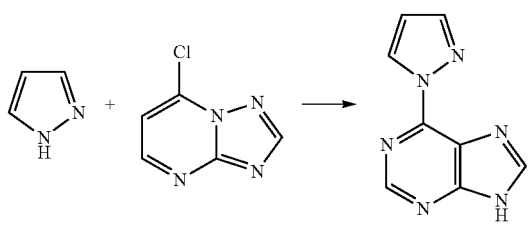 [SMILES: c1cn[nH]c1 ; Clc1ccnc2ncnn12 ; c1cnn(-c2ncnc3[nH]cnc23)c1]

300 mg of 7-chloro-[1,2,4]triazolo[1,5-a]pyrimidine and 700 mg of pyrazole are heated together to 120° C., forming a melt. After cooling, the batch is partially dissolved in methanol, the insoluble residue is separated off after 30 min. and dried in air.

HPLC: 1.384 min; MS: [187.1]; m.p. 191-193°;

$^1$H NMR (500 MHz, d$_6$-DMSO) δ [ppm] 9.43 (d, 1H, 2.8 Hz), 8.95 (d, 1H, J=5.0 Hz), 8.85 (s, 1H), 8.16 (d, 1H, J=1.5 Hz), 7.81 (d, 1H, J=5.0 Hz), 6.85 (dd, 1H, J=1.6 J=2.8 Hz).

EXAMPLE 3

The preparation of 5-[(R)-2-(naphthalen-1-yloxymethylpyrrolidin-1-yl]imidazo-[1,2-a]pyrimidine ("A3") is carried out analogously to the following scheme

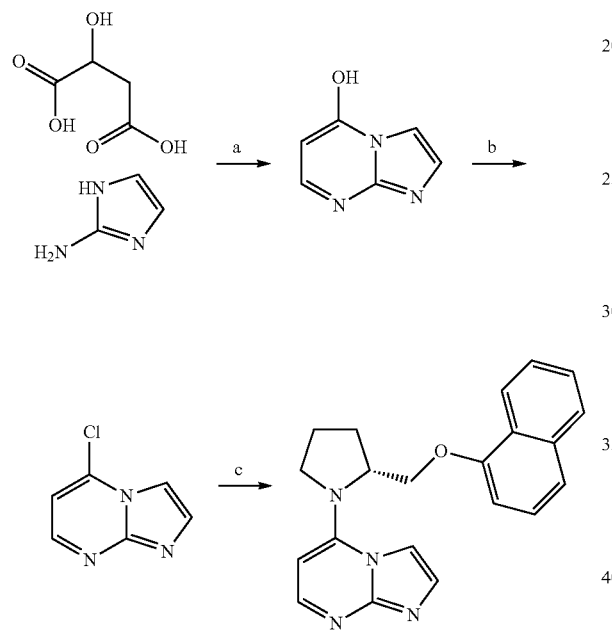

a)

9 g of malic acid and 5.6 g of 2-aminoimidazole are added to 25 ml of fuming sulfuric acid at 0° C. This solution is stirred at RT for 12 h and under reflux for one hour. For work-up, the batch is added to 100 g of ice and adjusted to pH=6 using conc. NaOH solution.

b)-c) analogous to Example 1

EXAMPLE 4

The preparation of 5-[(R)-2-(naphthalen-1-yloxymethyl)pyrrolidin-1-yl]-[1,2,4]-triazolo[4,3-a]pyrimidine ("A4") is carried out analogously to the following scheme

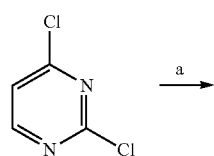

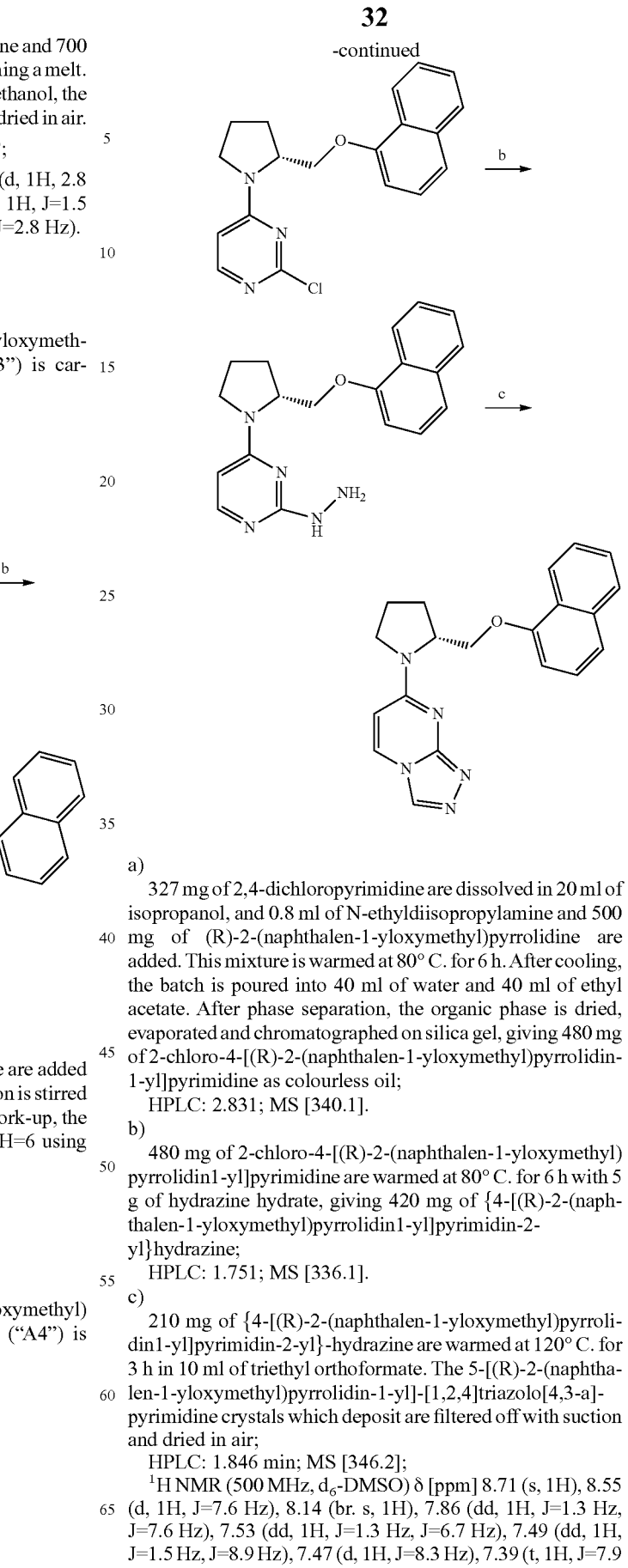

a)

327 mg of 2,4-dichloropyrimidine are dissolved in 20 ml of isopropanol, and 0.8 ml of N-ethyldiisopropylamine and 500 mg of (R)-2-(naphthalen-1-yloxymethyl)pyrrolidine are added. This mixture is warmed at 80° C. for 6 h. After cooling, the batch is poured into 40 ml of water and 40 ml of ethyl acetate. After phase separation, the organic phase is dried, evaporated and chromatographed on silica gel, giving 480 mg of 2-chloro-4-[(R)-2-(naphthalen-1-yloxymethyl)pyrrolidin-1-yl]pyrimidine as colourless oil;

HPLC: 2.831; MS [340.1].

b)

480 mg of 2-chloro-4-[(R)-2-(naphthalen-1-yloxymethyl)pyrrolidin1-yl]pyrimidine are warmed at 80° C. for 6 h with 5 g of hydrazine hydrate, giving 420 mg of {4-[(R)-2-(naphthalen-1-yloxymethyl)pyrrolidin1-yl]pyrimidin-2-yl}hydrazine;

HPLC: 1.751; MS [336.1].

c)

210 mg of {4-[(R)-2-(naphthalen-1-yloxymethyl)pyrrolidin1-yl]pyrimidin-2-yl}-hydrazine are warmed at 120° C. for 3 h in 10 ml of triethyl orthoformate. The 5-[(R)-2-(naphthalen-1-yloxymethyl)pyrrolidin-1-yl]-[1,2,4]triazolo[4,3-a]-pyrimidine crystals which deposit are filtered off with suction and dried in air;

HPLC: 1.846 min; MS [346.2];

$^1$H NMR (500 MHz, d$_6$-DMSO) δ [ppm] 8.71 (s, 1H), 8.55 (d, 1H, J=7.6 Hz), 8.14 (br. s, 1H), 7.86 (dd, 1H, J=1.3 Hz, J=7.6 Hz), 7.53 (dd, 1H, J=1.3 Hz, J=6.7 Hz), 7.49 (dd, 1H, J=1.5 Hz, J=8.9 Hz), 7.47 (d, 1H, J=8.3 Hz), 7.39 (t, 1H, J=7.9

Hz), 7.08 (br. s, 1H), 4.75 (br. s, 1H), 4.46 (br. s, 1H), 4.27 (br. s, 1H), 3.76 (br. m, 1H), 3.60 (br. s, 1H), 2.27 (br. m, 1H), 2.21 (br. m, 2H), 2.08 (br. m, 1H).

EXAMPLE 5

The preparation of 5-((R)-1-[1,2,4]triazolo[1,5-a]pyrimidin-7-ylpyrrolidin-2-ylmethoxy)quinoline ("A5") is carried out analogously to the following scheme

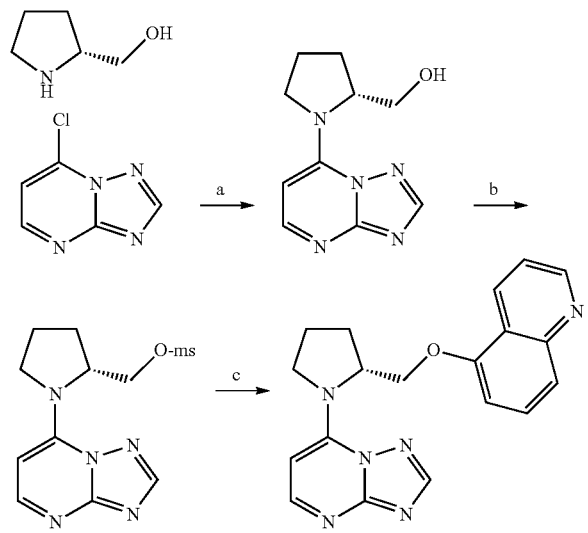

a)

1 g of commercially available (D)-prolinol, 1.5 g of 7-chloro-[1,2,4]triazolo-[1,5-a]pyrimidine and 2.6 g of N-ethyldiisopropylamine are heated at 130° C. in a microwave for 3 h in 60 ml of 1-butanol. The butanol is subsequently removed in vacuo, the residue is taken up in ethyl acetate, mixed with water, adjusted to pH 12 using 1 N NaOH solution, phases are separated, the organic phase is dried over sodium sulfate, evaporated and chromatographed on silica gel, giving 1.7 g of ((R)-1-[1,2,4]triazolo[1,5-a]pyrimidin-7-ylpyrrolidin-2-yl)methanol as beige crystals;

HPLC: 1.086 min; MS: [220.1].

b)

1.5 g of ((R)-1-[1,2,4]triazolo[1,5-a]pyrimidin-7-ylpyrrolidin-2-yl)methanol are dissolved in 15 ml of dichloromethane with stirring, and 1.9 ml of triethylamine are added. This solution is cooled to 0° C., and a solution of 0.8 ml of methanesulfonyl chloride in 5 ml of dichloromethane is added dropwise. When the addition is complete, the mixture is allowed to warm to RT for 12 h. For workup, the solution is poured into equal proportions by volume of water, the organic phase is extracted to exhaustion with ethyl acetate, the combined organic phases are dried over sodium sulfate, filtered off with suction, evaporated and chromatographed on silica gel, giving 1.1 g of ((R)-1-[1,2,4]triazolo-[1,5-a]pyrimidin-7-ylpyrrolidin-2-yl)methyl methanesulfonate as colourless oil;

HPLC: 1.424 min; MS [298.1].

c)

250 mg of ((R)-1-[1,2,4]triazolo[1,5-a]pyrimidin-7-ylpyrrolidin-2-yl)methyl methanesulfonate, 120 mg of 5-hydroxyquinoline and 1 g of caesium carbonate are suspended in 20 ml of DMF and stirred at 80° C. for 12 h. The solvent is subsequently stripped off in vacuo, the residue is partitioned between ethyl acetate and water, the organic phase is dried and purified by chromatography on silica gel, giving 90 mg of 5-[(R)-1-[1,2,4]triazolo[1,5-a]pyrimidin-7-ylpyrrolidin-2-ylmethoxyquinoline as beige crystals; HPLC: 1.312 min; MS [347.1]; m.p. 93-95°;

$^1$H NMR (500 MHz, d$_6$-DMSO) δ [ppm] 8.67 (d, 1H, J=5.2 Hz), 8.42 (s, 1H), 8.31 (d, 1H, J=5.6 Hz), 7.91 (d, 1H, J=9.0 Hz), 7.71 (m, 2H), 7.47 (ddd, 1H, J=1.0 Hz, J=6.8 Hz, J=7.8 Hz), 7.02 (d, 1H, J=5.2 Hz), 6.43 (d, 1H, J=5.6 Hz), 5.76 (br. m, 1H), 4.50 (dd, 1H, J=5.2 Hz, J=9.9 Hz), 4.32 (dd, 1H, J=6.3 Hz, J=9.9 Hz), 3.98 (m, 1H), 3.78 (m, 1H), 2.26 (m, 3H), 2.11 (m, 1H).

EXAMPLE 6

The preparation of 7-[2-(naphthalen-1-yloxymethyl)imidazol-1-yl]triazolo[1,5-a]-pyrimidine ("A6") is carried out analogously to the following scheme

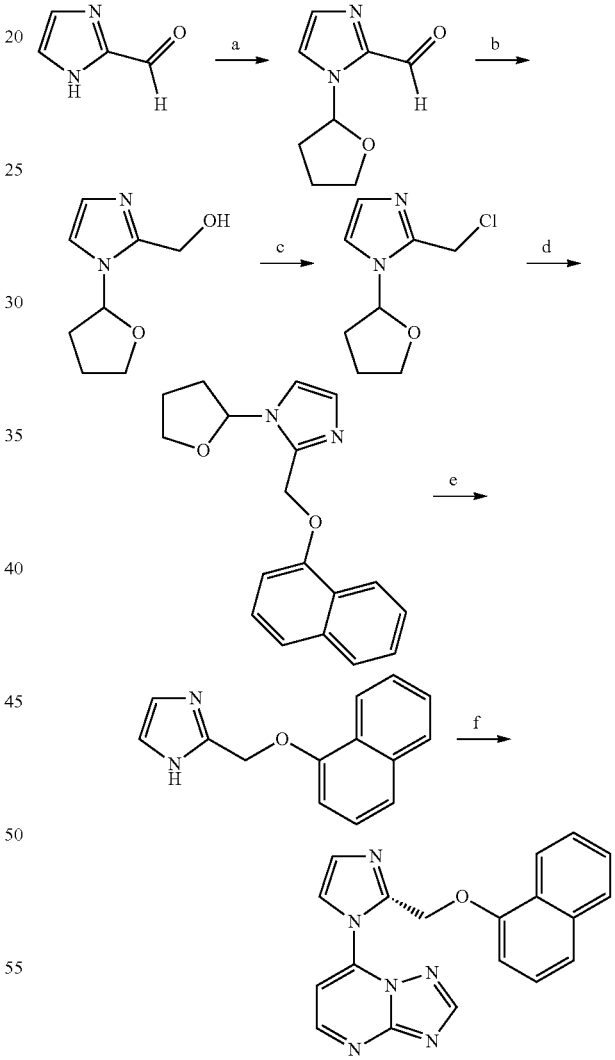

a)

5 g of imidazole-2-carboxaldehyde are heated under reflux for 12 h with 7 g of 2,3-dihydrofuran and 0.8 g of ptoluenesulfonic acid in 100 ml of THF. After cooling, the solvent is removed in vacuo, and the residue is partitioned between ethyl acetate and water. The organic phase is dried, filtered off, evaporated and purified on silica gel, giving 4.4 g of a yellow oil, which is detected as hydrate in the HPLC;

HPLC: 0.476; MS: [185.1].

b)

4.4 g of [1-(tetrahydrofuran-2-yl)-1H-imidazol-2-yl]carboxaldehyde are dissolved in 100 ml of methanol under nitrogen, and 1.9 g of sodium borohydride are added in portions. After 12 h, the reaction is complete, and the solvent is removed in vacuo. The residue is partitioned between water and ethyl acetate, the organic phase is dried, filtered off with suction and evaporated. The product is reacted further directly.

c)

2.8 g of [1-(tetrahydrofuran-2-yl)-1H-imidazol-2-yl]methanol are dissolved in 100 ml of dichloromethane under nitrogen, and 2.4 ml of thionyl chloride are added dropwise at 0° C. When the addition is complete, the mixture is allowed to warm to RT for 12 h. The precipitate of 2-chloromethyl)-1-(tetrahydrofuran-2-yl)-1H-imidazole hydrochloride which deposits is filtered off with suction, dried in air (1.6 g) and employed in the following reaction without further purification;

HPLC: 0.559; MS: [187.1].

d)

600 mg of 2-chloromethyl)-1-(tetrahydrofuran-2-yl)-1H-imidazole hydrochloride and 390 mg of 1-naphthol are stirred at 80° C. for 12 h with 1.2 g of potassium carbonate in 50 ml of DMF. The batch is partitioned between equal proportions of ethyl acetate and water, the organic phase is dried, filtered off, evaporated to dryness, and the resultant 500 mg of brown oil are reacted further directly; HPLC: 1.672; MS: [295.1].

e)

500 mg of 2-(naphthylen-1-yloxymethyl)-1-(tetrahydrofuran-2-yl)-1H-imidazole are warmed at 80° C. for 1 h with 1.3 ml of trifluoroacetic acid in 10 ml of 1,2-dichloroethane. The volatile constituents are removed in vacuo, giving 380 mg of 2-(naphthalen-1-yloxymethyl)-1H-imidazole, which is employed in the following reaction without further purification.

f) Analogous to the final step of Example 1, giving "A6".

The following compounds are obtained analogously to Examples 1-6

| Compound No. | Structure and/or name | M.p. [° C.] | HPLC-MS; rt; [M + H⁺]$ |
|---|---|---|---|
| "A8" | 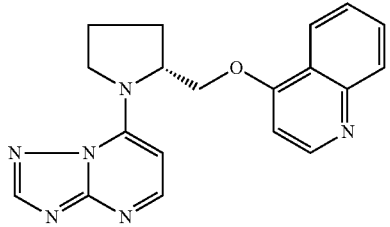<br>4-((R)-1-[1,2,4]Triazolo[1,5-a]pyrimidin-7-yl-pyrrolidin-2-ylmethoxy)quinoline | 156-157 | 1.475 min [347.1] |

$^1$H NMR (500 MHz, d$_6$-DMSO) δ [ppm] 8.86 (dd, 1H, J = 1.7 Hz, J = 4.2 Hz), 8.42 (s, 1H), 8.31 (d, 1H, J = 5.6 Hz), 8.09 (d, 1H, J = 8.2 Hz), 7.58 (m, 2H), 7.42 (dd, 1H, J = 4.2 Hz, J = 8.4 Hz), 7.05 (d, 1H, J = 7.58 Hz), 6.42 (d, 1H, J = 5.7 Hz), 5.72 (br. m, 1H), 4.43 (dd, 1H, J = 5.1 Hz, J = 9.8 Hz), 4.24 (dd, 1H, J = 6.5 Hz, J = 9.8 Hz), 3.99 (br. m, 1H), 3.79 (br. m, 1H), 2.25 (m, 3H), 2.10 (m, 1H).

| | | | |
|---|---|---|---|
| "A9" | 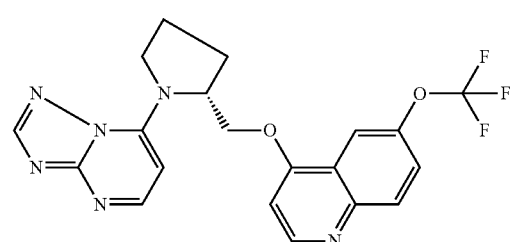<br>4-((R)-1-[1,2,4]Triazolo[1,5-a]pyrimidin-7-yl-pyrrolidin-2-ylmethoxy)-6-trifluoromethoxy-quinoline | 77-78 | 1.804 min [431.1] |

$^1$H NMR (500 MHz, d$_6$-DMSO) δ [ppm] 8.75 (d, 1H, J = 5.1 Hz), 8.38 (s, 1H), 8.30 (d, 1H, J = 5.6 Hz), 8.06 (d, 1H, J = 9.1 Hz), 7.71 (dd, 1H, J = 2.2 Hz, J = 9.2 Hz), 7.66 (s, 1H), 7.15 (d, 1H, J = 5.2 Hz), 6.44 (d, 1H, 5.6 Hz), 5.72 (br. m, 1H), 4.55 (dd, 1H, J = 5.2 Hz, J = 10.0 Hz), 4.37 (dd, 1H, J = 6.3 Hz, J = 10.0 Hz), 3.99 (br. m, 1H), 3.80 (br. m, 1H), 2.24 (m, 3H), 2.11 (m, 1H).

| Compound No. | Structure and/or name | M.p. [° C.] | HPLC-MS; rt; [M + H⁺]$ |
|---|---|---|---|
| "A10" | 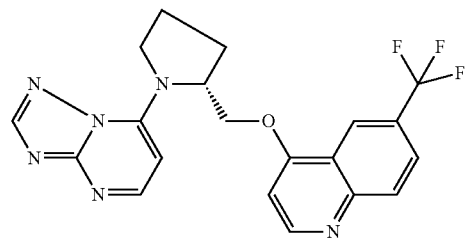<br>4-((R)-1-[1,2,4]Triazolo[1,5-a]pyrimidin-7-yl-pyrrolidin-2-ylmethoxy)-6-trifluoromethyl-quinoline | 171-172 | 1.806 min [415.1] |

$^1$H NMR (500 MHz, d$_6$-DMSO) δ [ppm] 8.85 (d, 1H, J = 5.2 Hz), 8.35 (s, 1H), 8.29 (d, 1H, J = 5.7 Hz), 8.18 (s, 1H), 8.12 (d, 1H, J = 8.8 Hz), 7.97 (dd, 1H, J = 2.0 Hz, J = 8.8 Hz), 7.23 (d, 1H, J = 5.3 Hz), 6.46 (d, 1H, J = 5.7 Hz), 5.72 (br. m, 1H), 4.58 (dd, 1H, J = 5.5 Hz, J = 10.1 Hz), 4.41 (dd, 1H, J = 6.6 Hz, J = 10.1 Hz), 4.01 (br. m, 1H), 3.82 (br. m, 1H), 2.25 (m, 3H), 2.11 (m, 1H).

| | | | |
|---|---|---|---|
| "A11" | 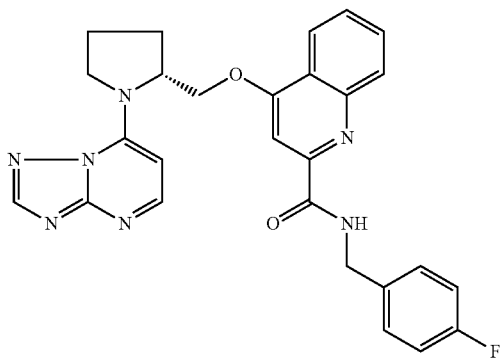<br>N-4-Fluorobenzyl-4-((R)-1-[1,2,4]triazolo-[1,5-a]pyrimidin-7-ylpyrrolidin-2-ylmethoxy)-quinoline-2-carboxamide | | 2.472 min [498.2] |

$^1$H NMR (500 MHz, d$_6$-DMSO) δ [ppm] 9.39 (t, 1H, J = 6.4 Hz), 8.48 (s, 1H), 8.31 (d, 1H, J = 5.6 Hz), 8.03 (d, 1H, J = 8.40 Hz), 7.81 (ddd, J = 1.2 Hz, J = 7.0 Hz, J = 8.3 Hz), 7.75 (d, 1H, J = 8.5 Hz), 7.73 (s, 1H), 7.57 (ddd, 1H, J = 0.8 Hz, J = 7.2 Hz, J = 7.9 Hz), 7.39 (dd, 2H, J = 5.6 Hz, J = 8.5 Hz), 7.14 (t, 2H, J = 8.9 Hz), 6.42 (d, 1H, J = 5.8 Hz), 5.79 (br. m, 1H), 4.64 (dd, 1H, J = 5.5 Hz, J = 10.0 Hz), 4.52 (d, 2H, J = 6.4 Hz), 4.43 (dd, 1H, J = 6.7 Hz, J = 10.0 Hz), 3.97 (br. m, 1H), 3.76 (br. m, 1H), 2.25 (m, 3H), 2.11 (m, 1H).

| Compound No. | Structure and/or name | M.p. [°C.] | HPLC-MS; rt; [M + H⁺]$ |
|---|---|---|---|
| "A12" | 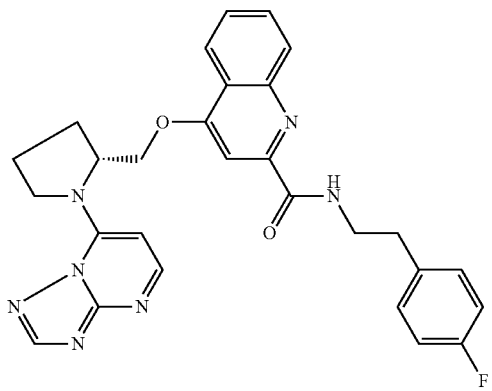<br>N-[2-(4-Fluorophenyl)ethyl]-4-((R)-1-[1,2,4]-triazolo[1,5-a]pyrimidin-7-ylpyrrolidin-2-yl-methoxy)quinoline-2-carboxamide | | 2.537 min [513.2] |
| | $^1$H NMR (500 MHz, d$_6$-DMSO) δ [ppm] 8.87 (t, 1H, J = 6.1 Hz), 8.47 (s, 1H), 8.31 (d, 1H, J = 5.4 Hz), 8.00 (d, 1H, J = 8.3 Hz), 7.81 (ddd, 1H, J = 1.4 Hz, J = 6.9 Hz, J = 8.3 Hz), 7.75 (d, 1H, J = 8.2 Hz), 7.71 (s, 1H), 7.56 (ddd, 1H, J = 1.1 Hz, J = 6.9 Hz, J = 8.2 Hz), 7.29 (dd, 2H, J = 5.6 Hz, J = 8.5 Hz), 7.10 (t, 2H, J = 8.9 Hz), 6.42 (d, 1H, J = 5.7 Hz), 5.78 (br. m, 1H), 4.64 (dd, 1H; J = 5.5 Hz, J = 10.2 Hz), 4.43 (dd, 1H, J = 6.7 Hz, J = 10.2 Hz), 3.97 (br. m, 1H), 3.76 (br. m, 1H), 3.57 (q, 2H, J = 6.5 Hz), 2.89 (t, 2H, J = 7.5 Hz), 2.26 (m, 3H), 2.11 (m, 1H). | | |
| "A13" | 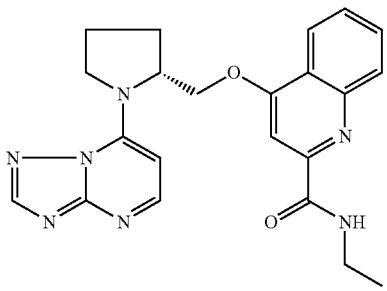<br>N-Ethyl-4-((R)-1-[1,2,4]triazolo[1,5-a]pyrimidin-7-ylpyrrolidin-2-ylmethoxy)quinoline-2-carboxamide | | 2.013 min [418.1] |
| | $^1$H NMR (500 MHz, d$_6$-DMSO) δ [ppm] 8.83 (t, 1H, J = 6.0 Hz), 8.48 (s, 1H), 8.31 (d, 1H, J = 5.7 Hz), 8.02 (d, 1H, J = 8.4 Hz), 7.80 (ddd, 1H, J = 1.3 Hz, J = 6.9 Hz, 8.3 Hz), 7.75 (d, 1H, J = 8.2 Hz), 7.72 (s, 1H), 7.56 (ddd, 1H, J = 0.9 Hz, J = 7.1 Hz, J = 8.0 Hz), 6.42 (d, 1H, J = 5.7 Hz), 5.78 (br. m, 1H), 4.64 (dd, 1H, J = 5.4 Hz, J = 10.0 Hz), 4.43 (dd, 1H, J = 6.7 Hz, J = 10.0 Hz), 3.97 (br. m, 1H), 3.77 (br. m, 1H), 3.37 (q, 2H, J = 7.2 Hz), 2.26 (m, 3H), 2.11 (m, 1H), 1.16 (t, 3H, J = 7.2 Hz). | | |

| Compound No. | Structure and/or name | M.p. [°C.] | HPLC-MS; rt; [M + H⁺]$ |
|---|---|---|---|
| "A14" | 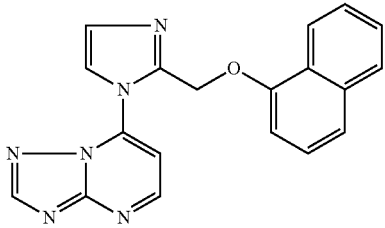<br>7-[2-(Naphthalen-1-yloxymethyl)imidazol-1-yl]-[1,2,4]triazolo[1,5-a]pyrimidine | 195-197 | 1.917 min [393.1] |

¹H NMR (500 MHz, d$_6$-DMSO) δ [ppm] 8.90 (d, 1H, J = 4.7 Hz), 8.71 (s, 1H), 7.84 (d, 1H, J = 1.5 Hz), 7.76 (d, 1H, J = 8.2 Hz), 7.72 (d, 1H, J = 4.7 Hz), 7.41 (m, 2H), 7.33 (t, 1H, J = 7.9 Hz), 7.31 (d, 1H, J = 1.5 Hz), 7.15 (ddd, 1H, J = 1.0 Hz, J = 6.9 Hz, J = 8.3 Hz), 7.00 (d, 1H, J = 7.5 Hz), 6.89 (d, 1H, J = 8.3 Hz), 5.54 (s, 2H).

| | | | |
|---|---|---|---|
| "A15" | 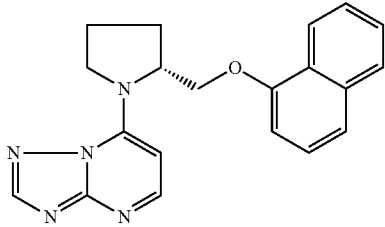<br>5-[(R)-2-(Naphthalen-1-yloxymethyl)pyrrolidin-1-yl]imidazo[1,2-a]pyrimidine | 115-117 | 1.776 min [345.1] |

¹H NMR (500 MHz, d$_6$-DMSO) δ [ppm] 8.19 (d, 1H, J = 5.2 Hz), 7.95 (d, 1H, J = 1.6 Hz), 7.80 (d, 1H, J = 8.2 Hz), 7.61 (d, 1H, J = 8.2 Hz), 7.57 (d, 1H, J = 1.6 Hz), 7.47 (ddd, 1H, J = 1.3 Hz, J = 6.8 Hz, J = 8.1 Hz), 7.41 (d, 1H, J = 8.2 Hz), 7.36 (ddd, 1H, J = 1.3 Hz, J = 6.9 Hz, J = 8.3 Hz), 7.31 (t, 1H, J = 7.8 Hz), 6.87 (d, 1H, J = 7.7 Hz), 6.48 (d, 1H, J = 5.2 Hz), 4.86 (m, 1H), 4.22 (dd, 1H, J = 5.4 Hz, J = 10.1 Hz), 4.15 (dd, 1H, J = 4.7 Hz, J = 10.1 Hz), 3.99 (ddd, 1H, J = 6.4 Hz, J = 9.3 Hz, J = 15.8 Hz), 3.72 (ddd, 1H, J = 2.3 Hz, J = 7.9 Hz, J = 9.6 Hz), 2.44 (m, 1H), 2.12 (m, 2H), 1.95 (m, 1H).

| | | | |
|---|---|---|---|
| "A16" | 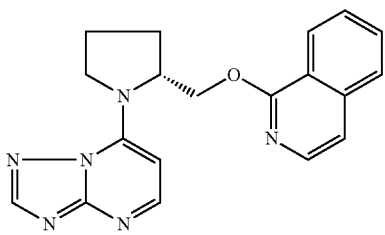<br>1-((R)-1-[1,2,4]Triazolo[1,5-a]pyrimidin-7-yl-pyrrolidin-2-ylmethoxy)isoquinoline | 72-74 | 2.195 min [347.1] |

¹H NMR (500 MHz, d$_6$-DMSO) δ [ppm] 8.33 (s, 1H), 8.27 (d, 1H, J = 5.7 Hz), 7.87 (d, 1H, J = 5.8 Hz), 7.85 (d, 1H, J = 8.5 Hz), 7.72 (m, 2H), 7.52 (ddd, 1H, J = 1.0 Hz, J = 7.1 Hz, J = 8.2 Hz), 7.34 (d, 1H, J = 5.7 Hz), 6.43 (d, 1H, 5.7 Hz), 5.64 (br. s, 1H), 4.64 (d, 2H, J = 5.5 Hz), 3.98 (br. s, 1H), 3.80 (br. m, 1H), 2.29-2.18 (m, 3H), 2.08 (m, 1H)

| Compound No. | Structure and/or name | M.p. [° C.] | HPLC-MS; rt; [M + H+]$ |
|---|---|---|---|
| "A17" | 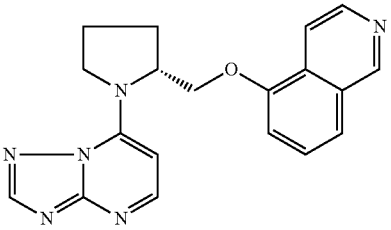<br>5-((R)-1-[1,2,4]Triazolo[1,5-a]pyrimidin-7-yl-pyrrolidin-2-ylmethoxy)isoquinoline | 158-159 | 1.408 min [347.1] |

$^1$H NMR (500 MHz, d$_6$-DMSO) δ [ppm] 9.24 (s, 1H), 8.41 (s. 1H), 8.31 (d, 1H, J = 5.7 Hz), 7.64 (d, 1H, J = 8.2 Hz), 7.54 (d, 1H; J = 8.2 Hz), 7.53 (d, 1H, J) = 11.1 Hz), 7.23 (d, 1H, J = 7.6 Hz), 6.43 (d, 1H, J = 5.7 Hz), 5.72 (br. s, 1H), 4.44 (dd, 1H, J = 5.1 Hz, J = 9.8 Hz), 4.23 (dd, 1H, J = 6.4 Hz, J = 9.8 Hz), 4.00 (br. s, 1H), 3.79 (br. m, 1H), 2.29 (m, 3H), 2.11 (m, 1H)

| Compound No. | Structure and/or name | M.p. [° C.] | HPLC-MS; rt; [M + H+]$ |
|---|---|---|---|
| "A18" | 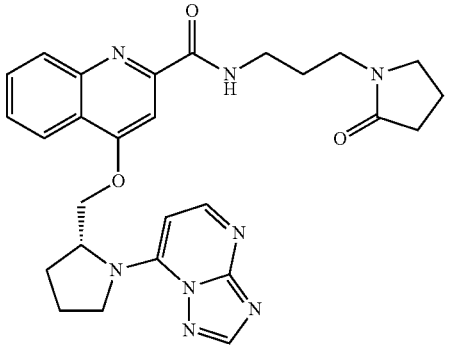<br>N-[3-(2-Oxopyrrolidin-1-yl)propyl]-4-((R)-1-[1,2,4]triazolo[1,5-a]pyrimidin-7-ylpyrrolidin-2-ylmethoxy)quinoline-2-carboxmide | | 1.845 min [515.2] |
| "A19" | 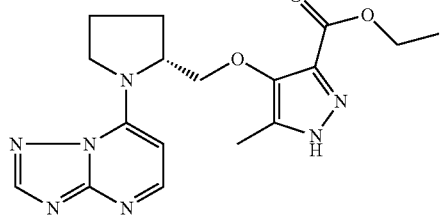<br>Ethyl 5-methyl-4-((R)-1-[1,2,4]triazolo[1,5-a]-pyrimidin-7-ylpyrrolidin-2-ylmethoxy)-1H-pyrazole-3-carboxylate | | 1.666 min [372.2] |

-continued

| Compound No. | Structure and/or name | M.p. [° C.] | HPLC-MS; rt; [M + H⁺]$ |
|---|---|---|---|
| "A20" | 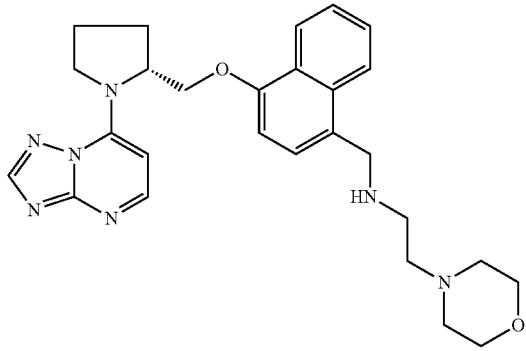<br>(2-Morpholin-4-ylethyl-[4-((R)-1-[1,2,4]-triazolo[1,5-a]pyrimidin-7-ylpyrrolidin-2-yl-methoxy)napthalen-1-ylmethyl]amine | | 1.498 min [488.3] |
| "A21" | 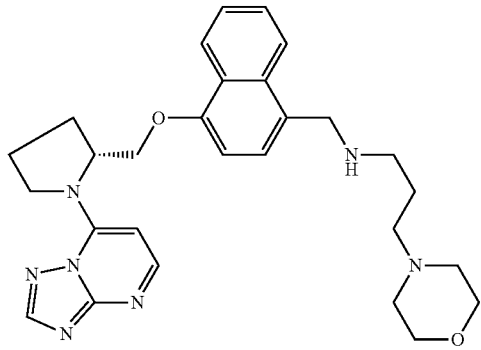<br>(3-Morpholin-4-ylpropyl)-[4-((R)-1-[1,2,4]-triazolo[1,5-a]pyrimidin-7-ylpyrrolidin-2-yl-methoxy)naphthalen-1-ylmethyl]amine | | 1.423 min [502.3] |
| "A22" | 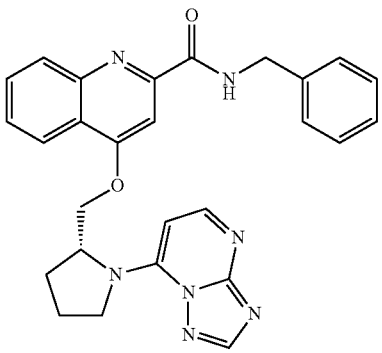<br>N-Benzyl-4-((R)-1-[1,2,4]triazolo[1,5-a]pyrimidin-7-ylpyrrolidin-2-ylmethoxy)quinoline-2-carboxmide | | 2.379 min [480.2] |

| Compound No. | Structure and/or name | M.p. [° C.] | HPLC-MS; rt; [M + H⁺]$ |
|---|---|---|---|
| "A23" | 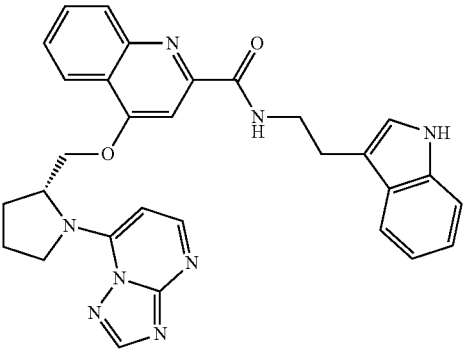<br>N-[2-(1H-Indol-3-yl)ethyl]-4-((R)-1-[1,2,4]-triazolo[1,5-a]pyrimidin-7-ylpyrrolidin-2-yl-methoxy)quinoline-2-carboxamide | | 2.336 min [533.2] |
| "A24" | 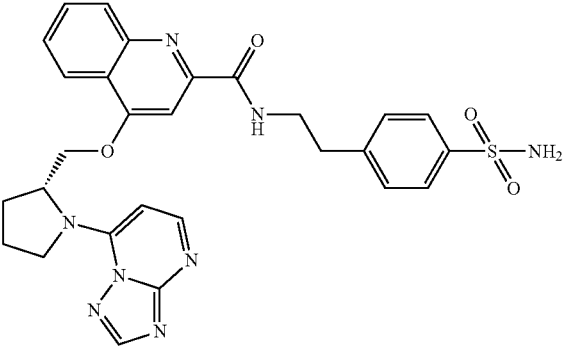<br>N-[2-(4-Sulfamoylphenyl)ethyl]-4-((R)-1-[1,2,4]-triazolo[1,5-a]pyrimidin-7-ylpyrrolidin-2-yl-methoxy)quinoline-2-carboxamide | | |
| "A25" | 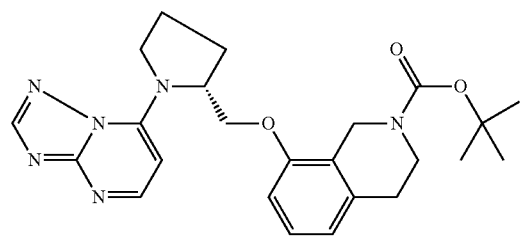<br>tert-Butyl 8-((R)-1-[1,2,4]triazolo[1,5-a]pyrimidin-7-ylpyrrolidin-2-ylmethoxy)-3,4-dihydro-1H-isoquinoline-2-carboxylate | | 2.492 min [451.2] |

¹H NMR (500 MHz, d₆-DMSO) δ [ppm] 8.39 (s, 1H), 8.29 (d, 1H, J = 5.6 Hz), 7.07 (t, 1H, J = 7.8 Hz), 6.78 (br. d, 1H, J = 7.7 Hz), 6.72 (d, 1H, J = 7.4 Hz), 6.37 (br. d, 1H, J = 5.5 Hz), 5.49 (br. m, 1H), 4.34 (m, 2H), 4.25 (m, 1H), 4.10 (m, 1H), 3.97 (m, 1H), 3.81 (m, 1H), 3.50, m 2H), 2.71 (m, 2H), 2.25-2.18 m, 3H), 2.07 (m, 1H), 1.44 (s, 9H)

| Compound No. | Structure and/or name | M.p. [° C.] | HPLC-MS; rt; [M + H+]$ |
|---|---|---|---|
| "A26" | 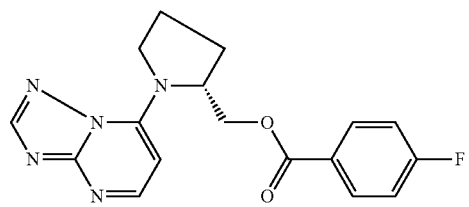<br>(R)-1-[1,2,4]Triazolo[1,5-a]pyrimidin-7-yl-pyrrolidin-2-ylmethyl 4-fluorobenzoate | | 2.020 min [342.1] |
| "A27" | 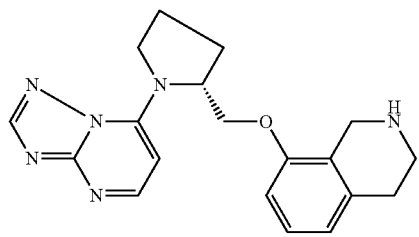<br>8-((R)-1-[1,2,4]Triazolo[1,5-a]pyrimidin-7-yl-pyrrolidin-2-ylmethoxy)-1,2,3,4-tetrahydro-isoquinoline | | 1.302 min [351.2] |

$^1$H NMR (500 MHz, d$_6$-DMSO) δ [ppm] 8.40 (s, 1H), 8.29 (d, 1H, J = 5.3 Hz), 6.98 (t, 1H, J = 7.8 Hz), 6.68 (d, 1H, J = 8.1 Hz), 6.62 (d, 1H, J = 7.5 Hz), 6.38 (d, 1H, J = 5.6 Hz), 5.54 (br. m, 1H), 4.16 (dd, 1H, J = 4.6 Hz, J = 9.8 Hz), 3.99 (dd, 1H, J = 5.9 Hz, J = 9.8 Hz), 3.94 (br. m, 1H), 3.77 (br. m, 1H), 3.50 (s, 2H), 2.83 (t, 2H, J = 5.7 Hz), 2.59 (t, 2H, J = 5.5 Hz), 2.23-2.17 (m, 2H), 2.15-2.10 (m, 1H), 2.05 (m, 1H)

| "A28" | 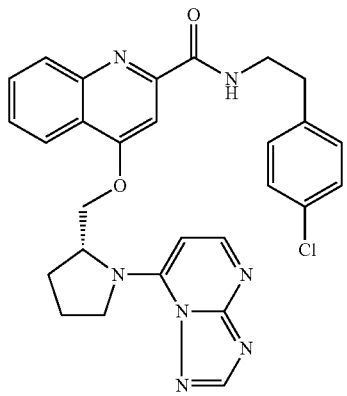<br>N-[2-(4-Chlorophenyl)ethyl]-4-((R)-1-[1,2,4]-triazolo[1,5-a]pyrimidin-7-ylpyrrolidin-2-yl-methoxy)quinoline-2-carboxamide | | |

-continued

| Compound No. | Structure and/or name | M.p. [° C.] | HPLC-MS; rt; [M + H⁺]$ |
|---|---|---|---|
| "A29" | 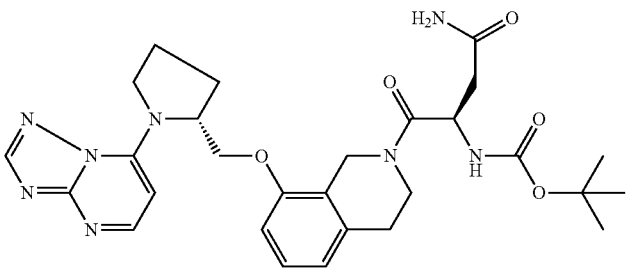<br>tert-Butyl {(R)-1-carbamoylmethyl-2-oxo-2-[8-((R)-1-[1,2,4]triazolo[1,5-a]pyrimidin-7-yl-pyrrolidin-2-ylmethoxy)-3,4-dihydro-1H-isoquinolin-2-yl]ethyl}carbamate | | 1.939 min [565.3] |
| "A30" | 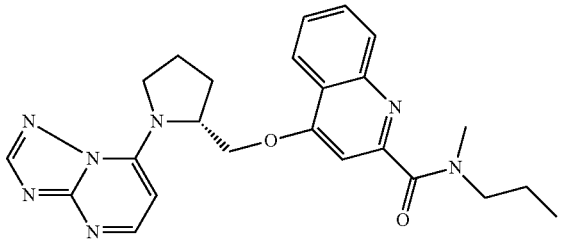<br>N-Ethylpropyl-4-((R)-1-[1,2,4]triazolo[1,5-a]-pyrimidin-7-ylpyrrolidin-2-ylmethoxy)quinoline-2-carboxamide | | |
| "A31" | 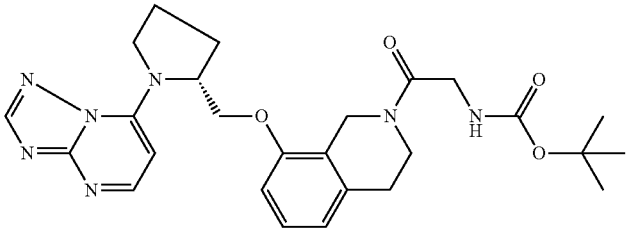<br>tert-Butyl {2-oxo-2-[8-((R)-1-[1,2,4]triazolo-[1,5-a]pyrimidin-7-ylpyrrolidin-2-ylmethoxy)-3,4-dihydro-1H-isoquinolin-2-yl]ethyl}carbamate | | 2.155 min [508.3] |
| "A32" | 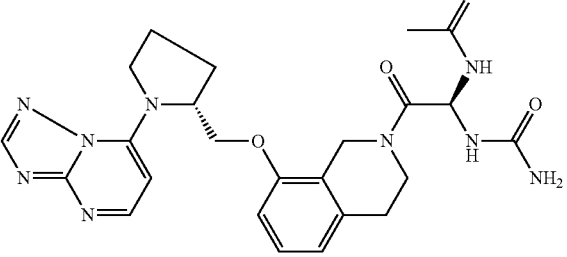<br>(S)-3-Acetylamino-4-oxo-4-[8-((R)-1-[1,2,4]-triazolo[1,5-a]pyrimidin-7-ylpyrrolidin-2-yl-methoxy)-3,4-dihydro-1H-isoquinolin-2-yl]-butyramide formate | | 1.583 min [507.2] |

| Com-pound No. | Structure and/or name | M.p. [° C.] | HPLC-MS; rt; [M + H+]$ |
|---|---|---|---|
| "A33" | 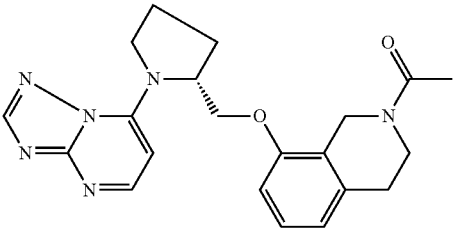<br>1-[8-((R)-1-[1,2,4]Triazolo[1,5-a]pyrimidin-7-yl-pyrrolidin-2-ylmethoxy)-3,4-dihydro-1H-isoquinolin-2-yl]ethanone | | 1.870 min [393.2] |
| "A34" | 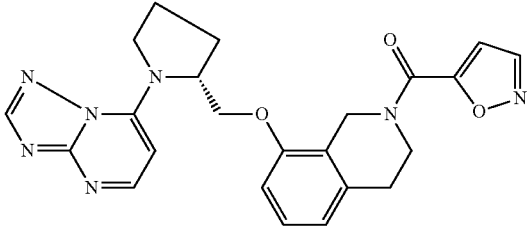<br>Isoxazol-5-yl-[8-((R)-1-[1,2,4]triazolo[1,5-a]-pyrimidin-7-ylpyrrolidin-2-ylmethoxy)-3,4-dihydro-1H-isoquinolin-2-yl]methanone<br>$^1$H NMR (500 MHz, d$_6$-DMSO) δ [ppm] 8.81 (d, 1H, J = 31 Hz), 8.39 (d, 1H, J = 9.6 Hz), 8.29 (dd, 1H, J = 5.7 Hz, J = 15.0 Hz), 7.12 (m, 1H), 7.00 (d, 1H, J = 5.7 Hz), 6.87 (d, 1H, J = 8.1 Hz), 6.77 (d, 1H, J = 7.7 Hz) | | 1.982 min [446.2] |
| "A35" | 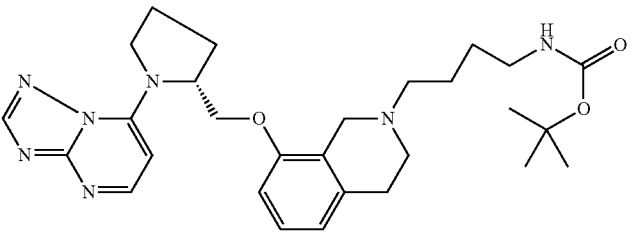<br>tert-Butyl {4-[8-((R)-1-[1,2,4]triazolo[1,5-a]-pyrimidin-7-ylpyrrolidin-2-ylmethoxy)-3,4-dihydro-1H-isoquinolin-2-yl]butyl}carbamate<br>$^1$H NMR (500 MHz, d$_6$-DMSO) δ [ppm] 8.40 (s, 1H), 8.30 (d, 1H, J = 5.7 Hz), 7.01 (dd, 1H, J = 7.7 Hz, J = 8.2 Hz), 6.82 (br. m, 1H), 6.70 (d, 1H, J = 8.2 Hz), 6.65 (d, 1H, J = 7.7 Hz), 6.39 (d, 1H, J = 5.7 Hz), 5.62 (br. m, 1H), 4.13 (dd, 1H, J = 5.4 Hz, J = 9.8 Hz), 4.02 (dd, 1H, J = 5.6 Hz, J = 9.8 Hz), 3.94 (br. m, 1H), 3.79 (br. m, 1H), 3.04 (m, 2H), 2.95 (m, 2H), 2.69 (m, 2H), 2.34 (m, 2H), 2.20 (m, 2H), 2.10 (m, 1H), 2.06 (m, 1H), 1.37 (s 9H) | | 1.665 min [522.3] |
| "A36" | 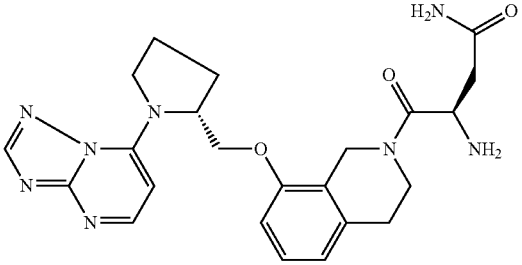<br>(R)-2-Amino-4-oxo-4-[8-((R)-1-[1,2,4]triazolo-[1,5-a]pyrimidin-7-ylpyrrolidin-2-ylmethoxy)-3,4-dihydro-1H-isoquinolin-2-yl]butyramide | | 1.389 min [465.2] |

| Compound No. | Structure and/or name | M.p. [°C.] | HPLC-MS; rt; [M + H+]$ |
|---|---|---|---|
| "A37" | 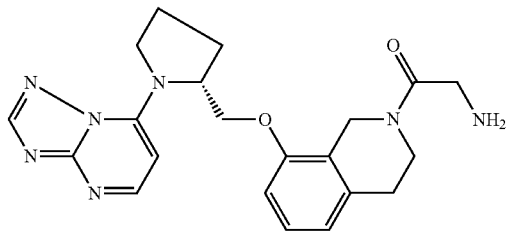<br>2-Amino-1-[8-((R)-1-[1,2,4]triazolo[1,5-a]-pyrimidin-7-ylpyrrolidin-2-ylmethoxy)-3,4-dihydro-1H-isoquinolin-2-yl]ethanone | | 1.419 min [408.2] |
| "A38" | 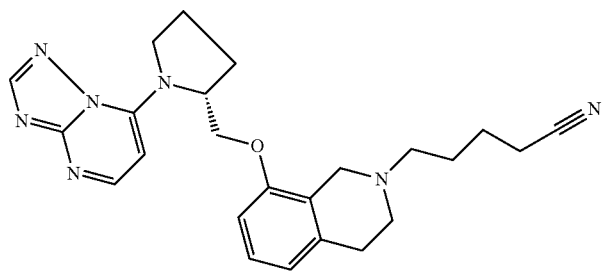<br>5-[8-((R)-1-[1,2,4]Triazolo[1,5-a]pyrimidin-7-yl-pyrrolidin-2-ylmethoxy)-3,4-dihydro-1H-isoquinolin-2-yl]pentanenitrile<br><br>$^1$H NMR (500 MHz, d$_6$-DMSO) δ [ppm] 8.41 (s, 1H), 8.31 (d, 1H, J = 5.5 Hz), 7.01 (dd, 1H, J = 7.6 Hz J = 8.0 Hz), 6.70 (d, 1H, J = 8.0 Hz), 6.65 (d, 1H, J = 7.6 Hz), 6.39 (d, 1H, J = 5.5 Hz), 5.67 (br. m, 1H), 4.11 (dd, 1H, J = 5.9 Hz, J = 9.8 Hz), 4.03 (dd, 1H, J = 5.6 Hz, J = 9.8 Hz), 3.94 (br. m, 1H), 3.77 (br. m, 1H), 2.98 (m, 2H), 2.69 (m, 2H), 2.56 (m, 2H), 2.36 (m, 2H), 2.20 (m, 2H), 2.07 (m, 2H), 1.61 (m, 2H), 1.53 (m, 2H) | | 1.422 min [432.25] |
| "A39" | 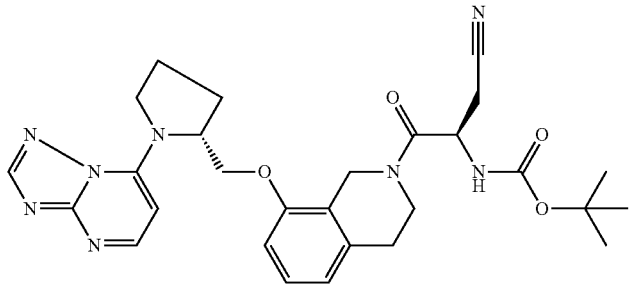<br>tert-Butyl {(R)-2-cyano-1-[8-((R)-1-[1,2,4]-triazolo[1,5-a]pyrimidin-7-ylpyrrolidin-2-yl-methoxy)-3,4-dihydro-1H-isoquinoline-2-carbonyl]ethyl}carbamate | | 2.177 min [547.3] |

-continued

| Compound No. | Structure and/or name | M.p. [°C.] | HPLC-MS; rt; [M + H+]$ |
|---|---|---|---|
| "A40" | 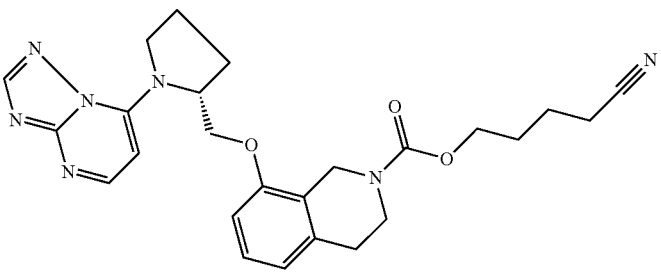

4-Cyanobutyl 8-((R)-1-[1,2,4]triazolo[1,5-a]-pyrimidin-7-ylpyrrolidin-2-ylmethoxy)-3,4-dihydro-1H-isoquinoline-2-carboxylate | | 2.138 min [476.2] |

¹H NMR (500 MHz, d₆-DMSO) δ [ppm] 8.39 (s, 1H), 8.23 (d, 1H, J = 5.7 Hz), 7.08 (dd, 1H, J = 7.6 Hz, J = 8.0 Hz), 6.80 (d, 1H, J = 8.0), 6.73 (d, 1H, J = 7.6 Hz), 6.38 (d, 1H, J = 5.7 Hz), 5.53 (br. m, 1H), 4.31 (m, 2H), 4.25 (m, 1H), 4.08 (m, 3H), 3.96 (m, 1H), 3.80 (m, 1H), 3.54 (m, 2H), 2.72 (m, 2H), 2.55 (m, 2H), 2.23 (m, 2H), 2.16 (m, 1H), 2.08 (m, 1H), 1.68 (m, 4H)

| "A41" | 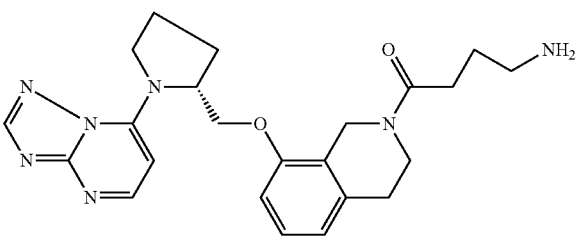

4-[8-((R)-1-[1,2,4]Triazolo[1,5-a]pyrimidin-7-yl-pyrrolidin-2-ylmethoxy)-3,4-dihydro-1H-isoquinolin-2-yl]butylamine | | 1.123 min [422.25] |

| "A42" | 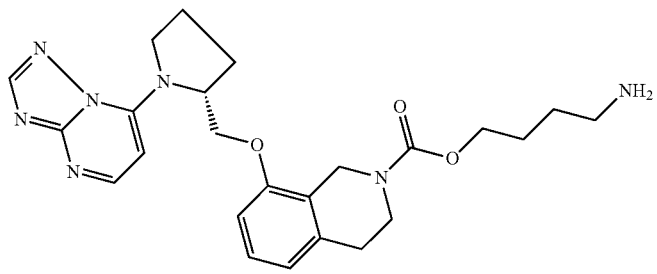

4-Aminobutyl 8-((R)-1-[1,2,4]triazolo[1,5-a]-pyrimidin-7-ylpyrrolidin-2-ylmethoxy)-3,4-dihydro-1H-isoquinoline-2-carboxylate | | 1.604 min [466.2] |

| "A43" | 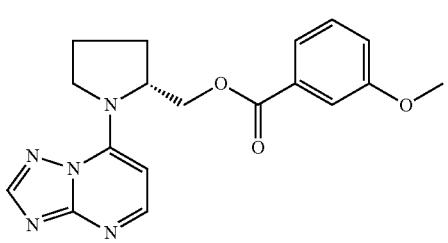

(R)-1-[1,2,4]Triazolo[1,5-a]pyrimidin-7-yl-pyrrolidin-2-ylmethyl 3-methoxybenzoate | | 1.966 min [354.2] |

¹H NMR (500 MHz, d₆-DMSO) δ [ppm] 8.41 (s, 1H), 8.36 (d, J = 5.6, 1H), 7.42 (t, J = 7.9, 1H), 7.32 (d, J = 7.7, 1H), 7.29-7.27 (m, 1H), 7.25 (ddd, J = 8.2, 2.7, 0.8, 1H), 6.47 (d, J = 5.6, 1H), 5.62 (m, 1H), 4.55 (dd, J = 11.3, 5.6, 1H), 4.47 (dd, J = 11.3, 5.5, 1H), 3.99 (m, 1H), 3.83 (d, J = 10.1, 5H), 3.35 (d, J = 11.9, 4H), 2.35-2.18 (m, 2H), 2.18-2.04 (m, 2H)

| Compound No. | Structure and/or name | M.p. [° C.] | HPLC-MS; rt; [M + H⁺]$ |
|---|---|---|---|
| "A44" | 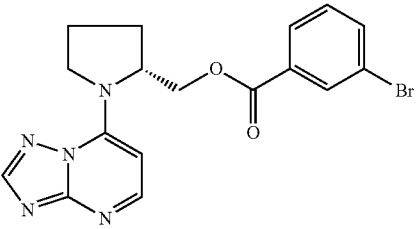<br>(R)-1-[1,2,4]Triazolo[1,5-a]pyrimidin-7-yl-pyrrolidin-2-ylmethyl 3-bromobenzoate | | 2.156 min [402.2 + 404.2] |

$^1$H NMR (500 MHz, $d_6$-DMSO) δ [ppm] 8.34 (s, 1H), 8.31 (d, J = 5.6, 1H), 7.87-7.81 (d, J = 8, 1H), 7.79 (s, 1H), 7.67 (d, J = 7.8, 1H), 7.42 (t, J = 7.9, 1H), 6.42 (d, J = 5.6, 1H), 5.58 (br. m, 1H), 4.51 (dd, J = 11.3, 5.7, 1H), 4.42 (dd, J = 11.3, 5.8, 1H), 3.95 (br. m, 1H), 3.77 (br. m, 1H), 2.32-2.13 (m, 2H), 2.13-1.98 (m, 2H)

| "A45" | 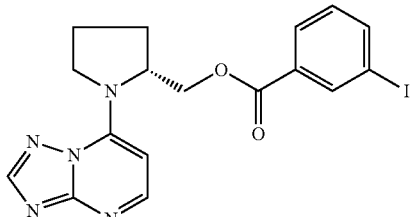<br>(R)-1-[1,2,4]Triazolo[1,5-a]pyrimidin-7-yl-pyrrolidin-2-ylmethyl 3-iodobenzoate | | 2.217 min [450.0] |

$^1$H NMR (500 MHz, $d_6$-DMSO) δ [ppm] 8.36 (d, J = 5.6, 1H), 8.07-8.00 (m, 2H), 7.73 (d, J = 7.8, 1H), 7.31 (t, J = 7.9, 1H), 6.47 (d, J = 5.7, 1H), 5.61 (s, 1H), 4.55 (dd, J = 11.3, 5.7, 1H), 4.46 (dd, J = 11.3, 5.8, 1H), 4.00 (s, 1H), 3.82 (t, J = 8.9, 1H), 2.35-2.16 (m, 2H), 2.16-2.04 (m, 2H)

| "A46" | 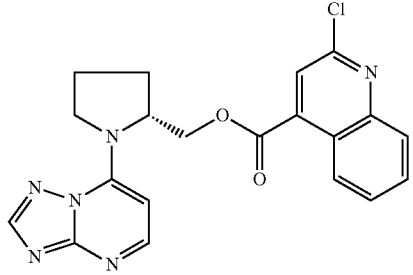<br>(R)-1-[1,2,4]Triazolo[1,5-a]pyrimidin-7-yl-pyrrolidin-2-ylmethyl 2-chloroquinoline-4-carboxylate | | 2.123 min [409.2] |

$^1$H NMR (500 MHz, $d_6$-DMSO) δ [ppm] 8.49 (d, J = 8.1, 1H), 8.32 (s, 1H), 8.30 (d, J = 5.6, 1H), 8.05 (d, J = 8.2, 1H), 7.94-7.88 (m, 1H), 7.75 (ddd, J = 8.3, 7.0, 1.2, 1H), 7.65 (s, 1H), 6.46 (d, J = 5.7, 1H), 5.57 (s, 1H), 4.66 (dd, J = 11.3, 5.8, 1H), 4.55 (dd, J = 11.3, 5.5, 1H), 4.00 (d, J = 12.4, 1H), 3.78 (dd, J = 17.1, 7.3, 1H), 2.31-2.20 (m, 1H), 2.19-2.10 (m, 2H), 2.10-1.99 (m, 1H)

| Compound No. | Structure and/or name | M.p. [° C.] | HPLC-MS; rt; [M + H⁺]$ |
|---|---|---|---|
| "A47" | 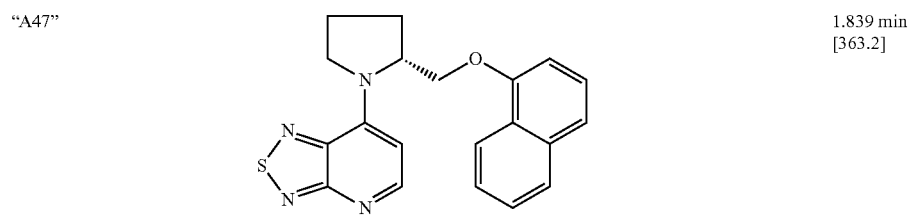

7-[(R)-2-(Naphthalen-1-yloxymethyl)pyrrolidin-1-yl]-1,2,5-thiadiazolo[3,4-b]pyridine | | 1.839 min [363.2] |
| | $^1$H NMR (500 MHz, d$_6$-DMSO) δ [ppm] 8.54 (d, J = 5.5, 1H), 7.93 (d, J = 7.8, 1H), 7.85 (d, J = 8.1, 1H), 7.54-7.49 (m, 1H), 7.45 (dd, J = 11.8, 4.7, 2H), 7.36 (t, J = 7.9, 1H), 6.96 (d, J = 7.6, 1H), 6.54 (d, J = 4.6, 1H), 5.52 (s, 1H), 4.42 (dd, J = 9.6, 4.3, 1H), 4.27 (dd, J = 9.6, 6.8, 1H), 3.98 (s, 1H), 3.76 (s, 1H), 2.43-2.24 (m, 3H), 2.18 (m, 1H). | | |
| "A48" | 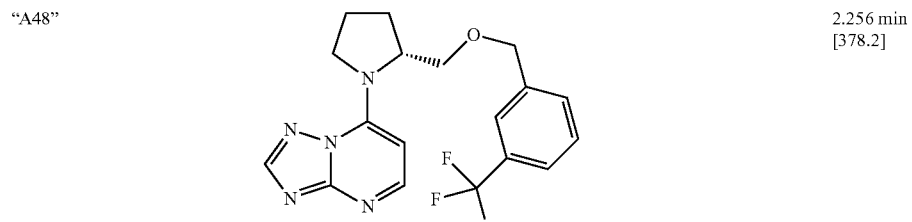

7-[(R)-2-(3-Trifluoromethylbenzyloxymethyl)-pyrrolidin-1-yl]-[1,2,4]triazolo[1,5-a]pyrimidine | | 2.256 min [378.2] |
| "A49" | 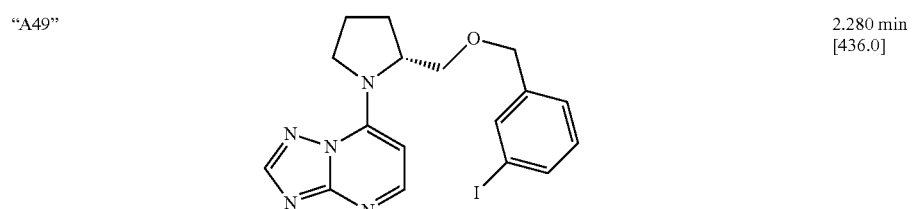

7-[(R)-2-(3-Iodobenzyloxymethyl)pyrrolidin-1-yl]-[1,2,4]triazolo[1,5-a]pyrimidine | | 2.280 min [436.0] |
| "A50" | 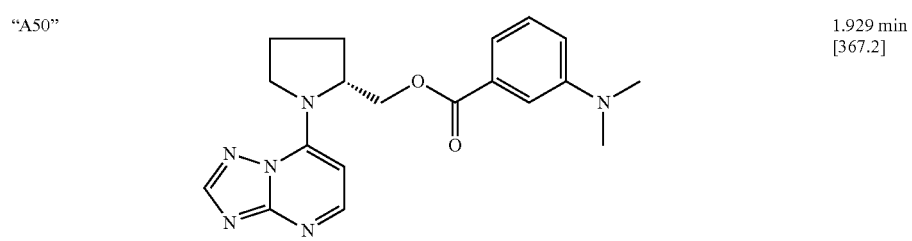

(R)-1-[1,2,4]Triazolo[1,5-a]pyrimidin-7-yl-pyrrolidin-2-ylmethyl 3-dimethylaminobenzoate | | 1.929 min [367.2] |

| Compound No. | Structure and/or name | M.p. [° C.] | HPLC-MS; rt; [M + H⁺]$ |
|---|---|---|---|
| "A51" | 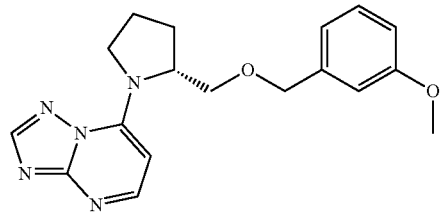<br>7-[(R)-2-(3-Methoxybenzyloxymethyl)pyrrolidin-1-yl]-[1,2,4]triazolo[1,5-a]pyrimidine | | 1.949 min [340.2] |

¹H NMR (400 MHz, d₆-DMSO) δ [ppm] 8.39 (s, 1H), 8.26 (d, J = 5.7, 1H), 7.17 (t, J = 7.1, 1H), 6.77 (m, 3H), 6.29 (d, J = 5.7, 1H), 5.23 (m, 1H), 4.46 (d, J = 12.5, 1H), 4.41 (d, J = 12.5, 1H), 4.12 (m, 1H), 3.88 (m, 1H), 3.70 (s, 3H), 3.61 (dd, J = 4.0; 9.7, 1H), 3.50 (dd, J = 6.5; 9.7, 2H), 2.09 (m, 3H), 1.98 (m, 1H)

| | | | |
|---|---|---|---|
| "A52" | 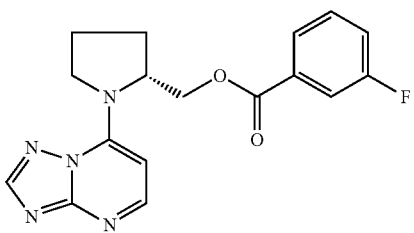<br>(R)-1-[1,2,4]Triazolo[1,5-a]pyrimidin-7-yl-pyrrolidin-2-ylmethyl 3-fluorobenzoate | | 1.968 min [342.2] |
| "A53" | 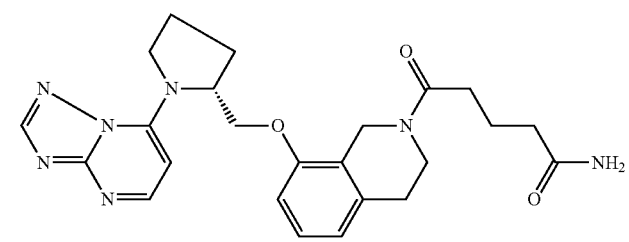<br>5-Oxo-5-[8-((R)-1-[1,2,4]triazolo[1,5-a]-pyrimidin-7-ylpyrrolidin-2-ylmethoxy)-3,4-dihydro-1H-isoquinolin-2-yl]pentanamide | | 1.709 min [464.3] |
| "A54" | 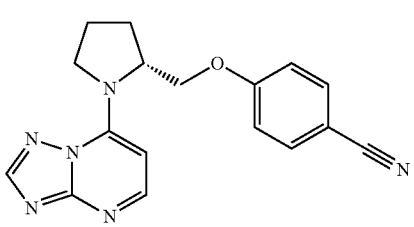<br>3-((R)-[1,2,4]Triazolo[1,5-a]pyrimidin-7-yl-pyrrolidin-2-ylmethoxymethyl)benzonitrile | | 1.861 min [335.2] |

¹H NMR (500 MHz, d₆-DMSO) δ [ppm] 8.36 (s, 1H), 8.26 (d, J = 5.7, 1H), 7.70 (d, J = 7.5, 1H), 7.65 (s, 1H), 7.52 (d, J = 7.9, 1H), 7.48 (t, J = 7.6, 1H), 6.30 (d, J = 5.7, 1H), 5.24 (d, J = 27.2, 1H), 4.54 (d, J = 12.9, 1H), 4.50 (d, J = 12.9, 1H), 3.87 (br. m, 1H), 3.75 (br. s, 1H), 3.65 (dd, J = 9.8, 4.2, 2H), 3.51 (dd, J = 9.8, 6.6, 2H), 2.15-2.03 (m, 3H), 2.04-1.92 (m, 1H)

| Compound No. | Structure and/or name | M.p. [° C.] | HPLC-MS; rt; [M + H⁺]$ |
|---|---|---|---|
| "A55" | 7-[(R)-2-(3-Fluorobenzyloxymethyl)pyrrolidin-1-yl]-[1,2,4]triazolo[1,5-a]pyrimidine | | 2.055 min [328.2] |
| | $^1$H NMR (500 MHz, d$_6$-DMSO) δ [ppm] 8.37 (s, 1H), 8.26 (d, J = 5.6, 1H), 7.35-7.26 (m, 1H), 7.10-6.95 (m, 3H), 6.30 (d, J = 5.7, 1H), 5.26 (s, 1H), 4.50 (d, J = 12.8, 1H), 4.46 (d, J = 12.8, 1H), 3.88 (s, 1H), 3.71 (s, 1H), 3.64 (dd, J = 9.7, 4.1, 1H), 3.50 (dd, J = 9.7, 6.6, 1H), 2.54-2.47 (m, 2H), 2.17-2.02 (m, 3H), 2.02-1.93 (m, 1H) | | |
| "A56" | 7-[(R)-2-(Pyridin-3-ylmethoxymethyl)pyrrolidin-1-yl]-[1,2,4]triazolo[1,5-a]pyrimidine | | 1.300 min [311.2] |
| "A57" | [2-((R)-[1,2,4]Triazolo[1,5-a]pyrimidin-7-yl-pyrrolidin-2-ylmethoxy)phenyl]acetic acid | | 1.722 min [354.1] |
| "A58" | 7-[(R)-2-(Pyridin-4-ylmethoxymethyl)pyrrolidin-1-yl]-[1,2,4]triazolo[1,5-a]pyrimidine | | 1.216 min [311.2] |
| "A59" | Methyl 2-((R)-[1,2,4]triazolo[1,5-a]pyrimidin-7-ylpyrrolidin-2-ylmethoxymethyl)-1H-indole-5-carboxylate | | 1.930 min [407.2] |

-continued

| Compound No. | Structure and/or name | M.p. [° C.] | HPLC-MS; rt; [M + H⁺]$ |
|---|---|---|---|
| "A60" | 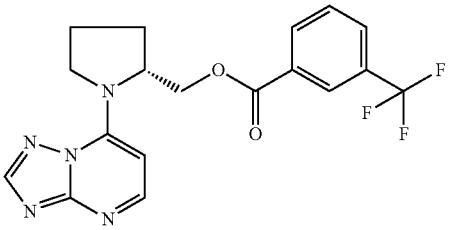<br>(R)-1-[1,2,4]Triazolo[1,5-a]pyrimidin-7-yl-pyrrolidin-2-ylmethyl 3-trifluoromethylbenzoate<br><br>$^1$H NMR (500 MHz, d$_6$-DMSO) δ [ppm] 8.32 (s, 1H), 8.29 (d, J = 5.6, 1H), 8.01 (d, J = 7.9, 1H), 7.95 (d, J = 7.9, 1H), 7.91 (s, 1H), 7.71 (t, J = 7.8, 1H), 6.42 (d, J = 5.7, 1H), 5.61 (br. m, 1H), 4.55 (dd, J = 11.3, 5.6, 1H), 4.45 (dd, J = 11.3, 6.0, 1H), 3.95 (br. m, 1H), 3.76 (br. m, 1H), 2.28-1.98 (m, 4H) | | 2.174 min [392.2] |
| "A61" | 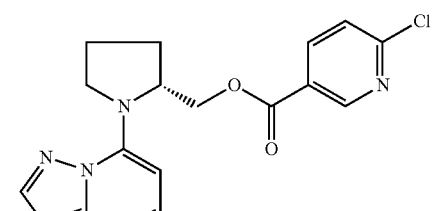<br>(R)-1-[1,2,4]Triazolo[1,5-a]pyrimidin-7-yl-pyrrolidin-2-ylmethyl 6-chloronicotinate<br><br>$^1$H NMR (500 MHz, d$_6$-DMSO) δ [ppm] 8.62 (d, J = 2.1, 1H), 8.34 (s, 1H), 8.30 (d, J = 5.7, 1H), 8.05 (dd, J = 8.3, 2.4, 1H), 7.62 (dd, J = 8.3, 0.6, 1H), 6.41 (d, J = 5.7, 1H), 5.53 (br. m, 1H), 4.54 (dd, J = 11.3, 5.6, 1H), 4.44 (dd, J = 11.3, 5.7, 1H), 3.94 (br. m, 1H), 3.74 (br. m, 1H), 2.27-1.99 (m, 4H) | | 1.794 min [359.0] |
| "A62" | 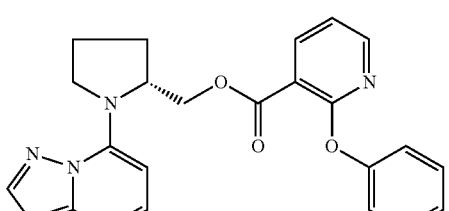<br>(R)-1-[1,2,4]Triazolo[1,5-a]pyrimidin-7-yl-pyrrolidin-2-ylmethyl 2-phenoxynicotinate<br><br>$^1$H NMR (500 MHz, d$_6$-DMSO) δ [ppm] 8.37 (s, 1H), 8.34-8.25 (m, 2H), 8.07 (dd, J = 7.6, 1.9, 1H), 7.42 (m, 2H), 7.27-7.14 (m, 2H), 7.07 (m, 2H), 6.36 (d, J = 5.7, 1H), 5.44 (br. m, 1H), 4.50 (dd, J = 11.4, 5.7, 1H), 4.44 (dd, J = 11.4, 4.6, 1H), 3.88 (br. m, 1H), 3.72 (br. m, 1H), 2.21-2.05 (m, 3H), 2.04-1.87 (m, 1H) | | 1.983 min [417.2] |
| "A63" | 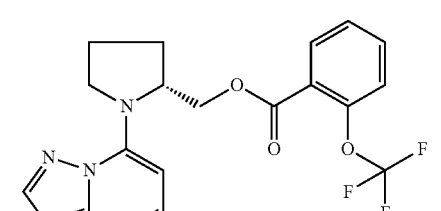<br>(R)-1-[1,2,4]Triazolo[1,5-a]pyrimidin-7-yl-pyrrolidin-2-ylmethyl 2-trifluoromethoxy-benzoate | | 2.055 min [328.2] |

| Compound No. | Structure and/or name | M.p. [° C.] | HPLC-MS; rt; [M + H⁺]$ |
|---|---|---|---|
| | ¹H NMR (500 MHz, d₆-DMSO) δ [ppm] 8.35 (s, 1H), 8.30 (d, J = 5.6, 1H), 7.79-7.65 (m, 2H), 7.53-7.43 (m, 2H), 6.38 (d, J = 5.7, 1H), 5.49 (br. m, 1H), 4.52-4.39 (m, 2H), 3.92 (br. m, 1H), 3.82-3.63 (m, 1H), 2.26-1.96 (m, 4H) | | |
| "A64" | 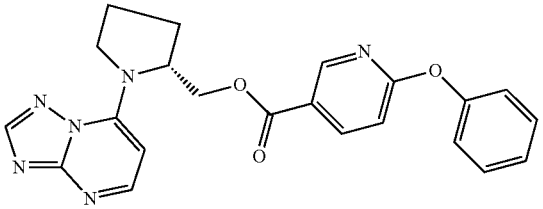<br>(R)-1-[1,2,4]Triazolo[1,5-a]pyrimidin-7-yl-pyrrolidin-2-ylmethyl 6-phenoxynicotinate | | 2.154 min [417.2] |
| | ¹H NMR (500 MHz, d₆-DMSO) δ [ppm] 8.48 (d, J = 1.8, 1H), 8.34 (s, 1H), 8.29 (d, J = 5.6, 1H), 8.05 (dd, J = 8.6, 2.1, 1H), 7.46 (m, 2H), 7.26 (m, 1H), 7.19 (d, J = 7.9, 2H), 7.05 (d, J = 8.6, 1H), 6.40 (d, J = 5.6, 1H), 5.52 (br. m, 1H), 4.49 (dd, J = 11.3, 5.5, 1H), 4.42 (dd, J = 11.3, 5.3, 1H), 3.89 (br. m, 1H), 3.74 (br. m, 1H), 2.23-2.02 (m, 4H) | | |
| "A65" | 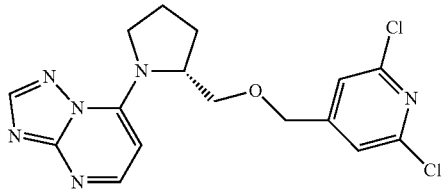<br>7-[(R)-2-(2,6-Dichloropyridin-4-ylmethoxy-methyl)pyrrolidin-1-yl]-[1,2,4]triazolo[1,5-a]-pyrimidine | | 2.084 min [381.0] |
| "A66" | 7-[(R)-2-(3-Bromobenzyloxymethyl)pyrrolidin-1-yl]-[1,2,4]triazolo[1,5-a]pyrimidine | | 2.257 min [388.0 + 390.0] |
| | ¹H NMR (500 MHz, d₆-DMSO) δ [ppm] 8.37 (s, 1H), 8.27 (d, J = 5.7, 1H), 7.46-7.38 (m, 2H), 7.27-7.13 (m, 2H), 6.29 (d, J = 5.7, 1H), 5.32 (br. m, 1H), 4.49 (d, J = 12.8, 1H), 4.45 (d, J = 12.8, 1H), 3.88 (br. m, 1H), 3.72 (br. m, 1H), 3.63 (dd, J = 9.7, 4.1, 1H), 3.50 (dd, J = 9.7, 6.6, 1H), 3.39 (br. m, 1H), 2.19-2.04 (m, 3H), 2.04-1.92 (m, 1H) | | |
| "A67" | 7-[(R)-2-(3-Trifluoromethoxybenzyloxymethyl)-pyrrolidin-1-yl]-[1,2,4]triazolo[1,5-a]pyrimidine<br>¹H NMR (500 MHz, d₆-DMSO) δ [ppm] 8.36 (s, 1H), 8.26 (d, J = 5.7, 1H), 7.41 (t, J = 7.9, 1H), 7.23 (d, J = 7.8, 2H), 7.19 (s, 1H), 6.30 (d, J = 5.7, 1H), 5.26 (br. m, 1H), 4.55 (d, J = 12.9, 1H), 4.50 (d, J = 12.9, 1H), 3.88 (br. m, 1H), 3.72 (br. m, 1H), 3.65 (dd, J = 9.8, 4.1, 2H), 3.52 (dd, J = 9.8, 6.6, 2H), 2.16-2.04 (m, 3H), 2.04-1.93 (m, 1H) | | 2.360 min [394.2] |
| "A68" | (R)-1-[1,2,4]Triazolo[1,5-a]pyrimidin-7-yl-pyrrolidin-2-ylmethyl 2-iodobenzoate<br>¹H NMR (500 MHz, d₆-DMSO) δ [ppm] 8.40 (s, 1H), 8.32 (d, J = 5.6, 1H), 8.00 (dd, J = 7.9, 0.7, 1H), 7.54-7.39 (m, 2H), 7.27 (td, J = 7.7, 1.9, 1H), 6.41 (d, J = 5.7, 1H), 5.49 (br. m, 1H), 4.47 (dd, J = 10.0, 4.7, 1H), 4.44 (dd, J = 10.0, 3.8, 1H), 3.97 (br. m, 1H), 3.83-3.68 (m, 1H), 2.29-2.10 (m, 3H), 2.09-1.99 (m, 1H) | | 2.124 min [450.0] |
| "A69" | (R)-1-[1,2,4]Triazolo[1,5-a]pyrimidin-7-yl-pyrrolidin-2-ylmethyl pyridine-2-carboxylate<br>¹H NMR (500 MHz, d₆-DMSO) δ [ppm] 8.62 (d, J = 4.6, 1H), 8.31 (s, 1H), 8.28 (d, J = 5.6, 1H), 7.92 (td, J = 7.7, 1.6, 1H), 7.81 (d, J = 7.8, 1H), 7.60 (dd, J = 7.1, 5.2, 1H), 6.38 (d, J = 5.6, 1H), 5.60 (br. m, 1H), 4.55 (dd, J = 11.3, 5.7, 1H), 4.42 (dd, J = 11.3, 5.4, 1H), 3.91 (br. m, 1H), 3.80-3.65 (m, 1H), 2.32-2.15 (m, 2H), 2.15-1.98 (m, 2H) | | 1.443 min [325.2] |

| Compound No. | Structure and/or name | M.p. [° C.] | HPLC-MS; rt; [M + H+]$ |
|---|---|---|---|
| "A70" | 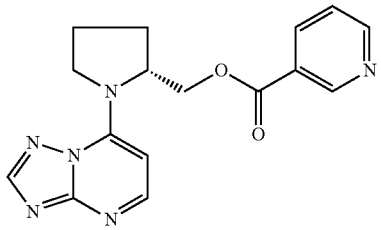<br>(R)-1-[1,2,4]Triazolo[1,5-a]pyrimidin-7-yl-pyrrolidin-2-ylmethyl nicotinate<br><br>$^1$H NMR (500 MHz, d$_6$-DMSO) δ [ppm] 8.85 (d, J = 1.7, 1H), 8.79 (dd, J = 4.8, 1.6, 1H), 8.35 (s, 1H), 8.31 (d, J = 5.6, 1H), 8.02 (dt, J = 7.9, 1.8, 1H), 7.50 (dd, J = 7.9, 4.9, 1H), 6.42 (d, J = 5.7, 1H), 5.58 (br. m, 1H), 4.53 (dd, J = 11.3, 5.7, 1H), 4.46 (dd, J = 11.3, 5.5, 1H), 3.96 (br. m, 1H), 3.76 (br. m, 1H), 2.30-1.97 (m, 4H) | | 1.489 min [325.2] |
| "A71" | (R)-1-[1,2,4]Triazolo[1,5-a]pyrimidin-7-yl-pyrrolidin-2-ylmethyl benzoate | | 1.917 min [324.2] |
| "A72" | (R)-1-[1,2,4]Triazolo[1,5-a]pyrimidin-7-yl-pyrrolidin-2-ylmethyl 3-ethoxybenzoate<br>$^1$H NMR (500 MHz, d$_6$-DMSO) δ [ppm] 8.36 (s, 1H), 8.31 (d, J = 5.6, 1H), 7.35 (t, J = 7.9, 1H), 7.25 (d, J = 7.7, 1H), 7.24-7.14 (m, 2H), 6.42 (d, J = 5.7, 1H), 5.56 (br. m, 1H), 4.49 (dd, J = 11.3, 5.7, 1H), 4.41 (dd, J = 11.3, 5.5, 1H), 4.02 (q, J = 7.0, 3H), 3.95 (br. m, 1H), 3.83-3.71 (m, 1H), 2.29-2.13 (m, 2H), 2.07 (m, 2H), 1.34 (t, J = 7.0, 4H) | | 2.111 min [368.2] |
| "A73" | (R)-1-[1,2,4]Triazolo[1,5-a]pyrimidin-7-yl-pyrrolidin-2-ylmethyl 5-chloro-2-fluorobenzoate<br>$^1$H NMR (500 MHz, d$_6$-DMSO) δ [ppm] 8.34 (s, 1H), 8.31 (d, J = 5.6, 1H), 7.78-7.70 (m, 1H), 7.61 (dd, J = 6.1, 2.7, 1H), 7.43-7.30 (m, 1H), 6.41 (d, J = 5.7, 1H), 5.54 (br. m, 1H), 4.52 (dd, J = 11.3, 5.7, 1H), 4.42 (dd, J = 11.3, 5.5, 1H), 3.95 (br. m, 1H), 3.84-3.65 (m, 1H), 2.26-2.13 (m, 2H), 2.13-1.97 (m, 2H) | | 2.086 min [376.0] |
| "A74" | (R)-1-[1,2,4]Triazolo[1,5-a]pyrimidin-7-yl-pyrrolidin-2-ylmethyl 3-chloromethylbenzoate | | 2.059 min [372.0] |
| "A75" | 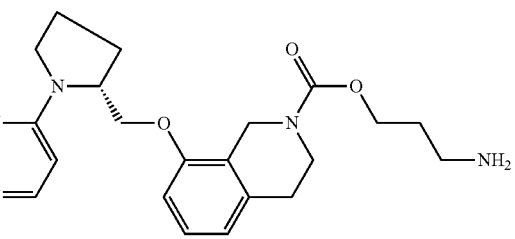<br>3-Aminopropyl 8-((R)-1-[1,2,4]Triazolo[1,5-a]-pyrimidin-7-ylpyrrolidin-2-ylmethoxy)-3,4-dihydro-1H-isoquinoline-2-carboxylate | | 1.570 min [452.2] |
| "A76" | 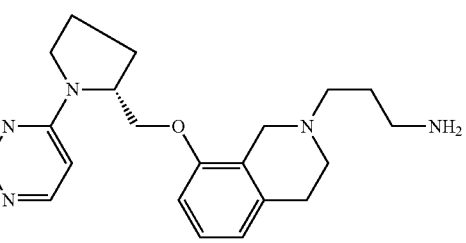<br>3-[8-((R)-1-[1,2,4]Triazolo[1,5-a]pyrimidin-7-yl-pyrrolidin-2-ylmethoxy)-3,4-dihydro-1H-isoquinoline-2-yl]propylamine | | 1.181 min [408.3] |

| Compound No. | Structure and/or name | M.p. [° C.] | HPLC-MS; rt; [M + H⁺]$ |
|---|---|---|---|
| "A77" | 7-[(R)-2-(Naphthalen-1-yloxymethyl)pyrrolidin-1-yl]-[1,2,4]triazolo[1,5-a]-1,3,5-triazine<br>¹H NMR (500 MHz, d₆-DMSO) δ [ppm] 8.51 (s, 1H), 8.38 (s, 1H), 7.70 (d, J = 7.9, 1H), 7.46-7.31 (m, 4H), 7.26 (m, 1H), 6.85 (m, 1H), 5.80 (br. m, 1H), 5.00 (br. m, 1H), 4.50 (m, 1H) 4.41 (dd, J = 9.6, 3.4, 1H), 4.35 (br. m 1H), 2.25 (m, 3H), 2.07 (m, 1H) | | 2.450 min [347.1] |
| "A78" | 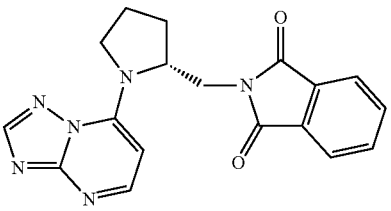<br>2-((R)-1-[1,2,4]Triazolo[1,5-a]pyrimidin-7-yl-pyrrolidin-2-ylmethyl)isoindole-1,3-dione | | 1.697 min [349.2] |
| "A79" | (R)-1-[1,2,4]Triazolo[1,5-a]pyrimidin-7-yl-pyrrolidin-2-ylmethyl 3-cyanobenzoate | | 1.829 min [349.2] |
| "A80" | 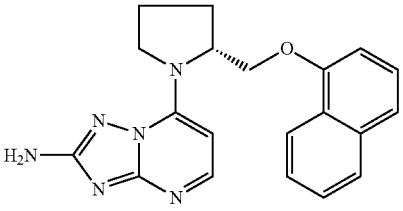<br>7-[(R)-2-(Naphthalen-1-yloxymethyl)pyrrolidin-1-yl]-[1,2,4]triazolo[1,5-a]pyrimidin-2-ylamine | 235-236 | 2.055 min [361.1] |
| "A81" | 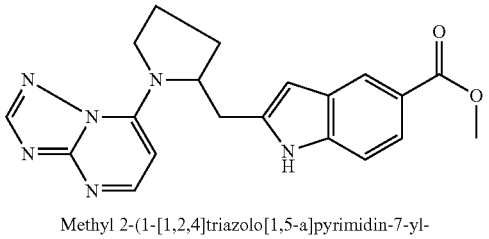<br>Methyl 2-(1-[1,2,4]triazolo[1,5-a]pyrimidin-7-yl-pyrrolidin-2-ylmethyl)-1H-indole-5-carboxylate<br>¹H NMR (500 MHz, d₆-DMSO) δ [ppm] 11.42 (s, 1H), 8.44 (s, 1H) 8.30 (d, J = 5.7, 1H), 8.14 (d, J = 15.1, 1H), 7.68 (dd, J = 8.5, 1.5, 1H), 7.41 (d, J = 8.5, 1H), 6.49-6.33 (m, 2H), 5.24 (br. m, 1H), 4.01 (br. m, 1H), 3.83 (s, 3H), 3.23 (dd, J = 14.4, 3.2, 1H), 3.06 (dd, J = 14.4, 7.2, 2H), 2.93 (dd, J = 14.4, 9.7, 1H) 2.07-1.81 (m, 4H), 1.25-1.11 (m, 2H) | | 2.023 min [377.2] |
| "A82" | (R)-1-[1,2,4]Triazolo[1,5-a]pyrimidin-7-yl-pyrrolidin-2-ylmethyl 3-trifluoromethoxy-benzoate<br>¹H NMR (500 MHz, d₆-DMSO) δ [ppm] 8.33 (s, 1H), 8.29 (d, J = 5.6, 1H), 7.69 (br. d, J = 7.6, 1H), 7.65 (br. d, J = 8.2, 1H), 7.61 (d, J = 7.8, 1H), 7.58 (m, 1H), 6.41 (d, J = 5.7, 1H), 5.58 (s, 1H), 4.51 (dd, J = 11.3, 5.7, 1H), 4.44 (dd, J = 11.3, 5.7, 1H), 3.95 (br. m, 1H), 3.75 (br. m, 1H), 2.27-2.00 (m, 4H) | | 2.251 min [408.2] |

| Compound No. | Structure and/or name | M.p. [° C.] | HPLC-MS; rt; [M + H+]$ |
|---|---|---|---|
| "A83" | 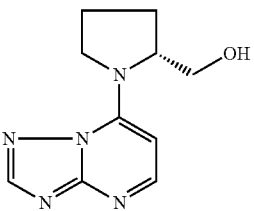<br>((R)-1-[1,2,4]Triazolo[1,5-a]pyrimidin-7-yl-pyrrolidin-2-yl)methanol | 168-170 | 1.094 min [220.1] |
| | $^1$H NMR (500 MHz, d$_6$-DMSO) δ [ppm] 8.37 (s, 1H), 8.27 (t, J = 6.6, 1H), 6.30 (d, J = 5.7, 1H), 4.94 (s, 1H), 4.87 (t, J = 5.7, 1H), 3.96 (s, 1H), 3.79 (d, J = 6.3, 1H), 3.57 (ddd, J = 10.8, 5.4, 3.9, 1H), 3.45 (dt, J = 11.0, 6.3, 1H), 2.15-2.01 (m, 3H), 2.00-1.91 (m, 1H) | | |
| "A84" | 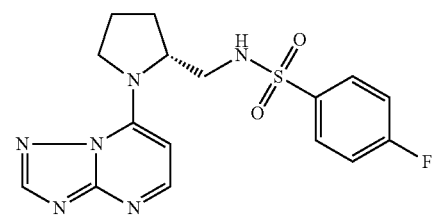<br>4-Fluoro-N-((R)-1-[1,2,4]triazolo[1,5-a]-pyrimidin-7-ylpyrrolidin-2-ylmethyl)benzene-sulfonamide | | 1.721 min [377.1] |
| | $^1$H NMR (500 MHz, d$_6$-DMSO) δ [ppm] 8.32 (s, 1H), 8.25 (d, J = 5.7, 1H), 7.97 (t, J = 6.4, 1H), 7.88-7.73 (m, 2H), 7.47-7.30 (m, 2H), 6.22 (d, J = 5.8, 1H), 4.88 (br. m, 1H), 3.94 (br. m, 1H), 3.76 (br. m, 1H), 3.06 (ddd, J = 13.3, 5.9, 3.7, 1H), 3.01-2.88 (m, 1H), 2.14-1.89 (m, 4H) | | |
| "A85" | 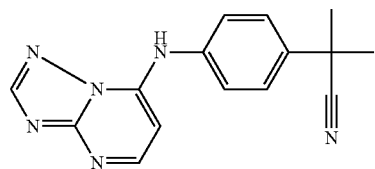<br>2-Methyl-2-[4-([1,2,4]triazolo[1,5-a]pyrimidin-7-ylamino)phenyl]propionitrile | | 1.718 min [279.2] |
| | $^1$H NMR (500 MHz, d$_6$-DMSO) δ [ppm] 8.82 (s, 1H), 8.45 (d, J = 6.0, 1H), 7.67 (d, J = 8.7, 2H), 7.54 (d, J = 8.7, 2H), 6.63 (d, J = 6.0, 3H), 1.74 (s, 6H) | | |
| "A86" | 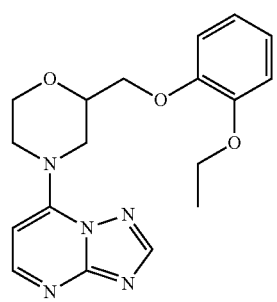<br>7-[2-(2-Ethoxyphenoxymethyl)morpholin-4-yl]-[1,2,4]triazolo[1,5-a]pyrimidine | | 1.939 min [356.2] |
| | $^1$H NMR (500 MHz, d$_6$-DMSO) δ [ppm] 8.52 (s, 1H), 7.03 (dd, J = 7.5, 2.0, 1H), 6.98 (dd, J = 7.7, 1.9, 1H), 6.95-6.84 (m, 1H), 6.68 (d, J = 5.5, 1H), 4.68 (d, J = 12.7, 1H), 4.53 (d, J = 12.7 1H), 4.16-4.09 (m, 1H), 4.08-4.00 (m, 4H), 3.80 (td, J = 11.6, 2.5, 1H), 3.30-3.16 (m, 1H), 1.32 (t, J = 7.0, 2H) | | |

| Compound No. | Structure and/or name | M.p. [° C.] | HPLC-MS; rt; [M + H+]$ |
|---|---|---|---|
| "A87" | 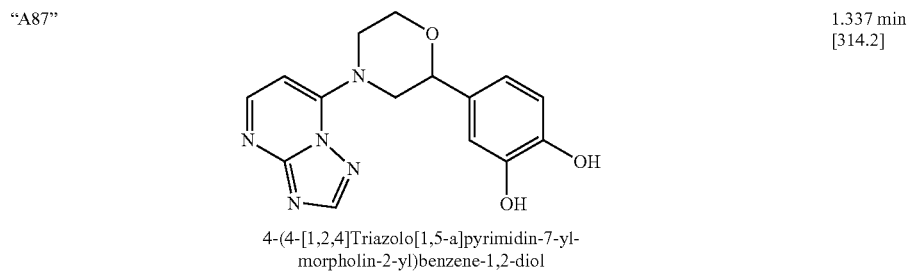<br>4-(4-[1,2,4]Triazolo[1,5-a]pyrimidin-7-yl-morpholin-2-yl)benzene-1,2-diol | | 1.337 min [314.2] |

$^1$H NMR (500 MHz, d$_6$-DMSO) δ [ppm] 8.86 (br. s, 2H), 8.52 (s, 1H), 8.48 (d, J = 5.5, 1H), 6.83 (d, J = 1.8, 1H), 6.79-6.63 (m, 3H), 4.66 (d, J = 12.8, 1H), 4.55 (dd, J = 10.5, 2.3, 1H), 4.50 (br. d, J = 12.9, 1H), 4.11 (dd, J = 11.8, 2.0, 1H), 3.86 (td, J = 11.7, 2.4, 1H), 3.12 (dd, J = 12.7, 10.6, 1H)

| | | | |
|---|---|---|---|
| "A88" | 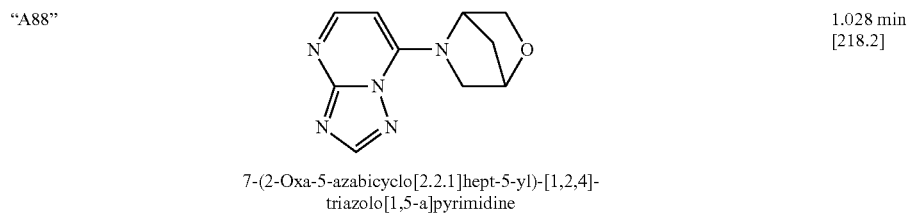<br>7-(2-Oxa-5-azabicyclo[2.2.1]hept-5-yl)-[1,2,4]-triazolo[1,5-a]pyrimidine | | 1.028 min [218.2] |

$^1$H NMR (500 MHz, d$_6$-DMSO) δ [ppm] 8.40 (s, 1H), 8.29 (d, J = 5.6, 1H), 6.33 (s, 1H), 4.76 (s, 1H), 3.86 (dt, J = 7.8, 4.6, 3H), 3.34 (br. m, 5H), 2.07 (dd, J = 10.2, 2.1, 1H), 1.98 (d, J = 10.2, 1H)

| | | | |
|---|---|---|---|
| "A89" | 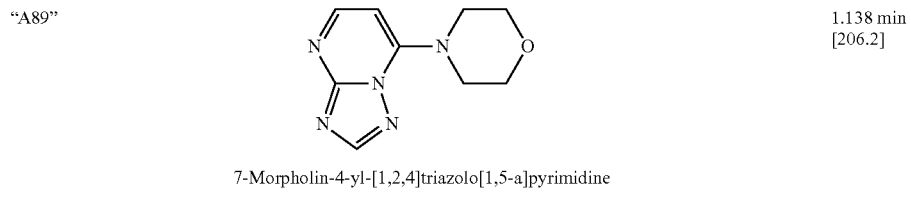<br>7-Morpholin-4-yl-[1,2,4]triazolo[1,5-a]pyrimidine | | 1.138 min [206.2] |

$^1$H NMR (500 MHz, d$_6$-DMSO) δ [ppm] 8.52 (s, 1H), 8.50 (d, J = 5.5, 1H), 6.65 (d, J = 5.5, 1H), 3.88 (dd, J = 5.8, 3.5, 5H), 3.81 (dd, J = 5.7, 3.4, 5H), 3.34 (br. m, 5H)

| | | | |
|---|---|---|---|
| "A90" | 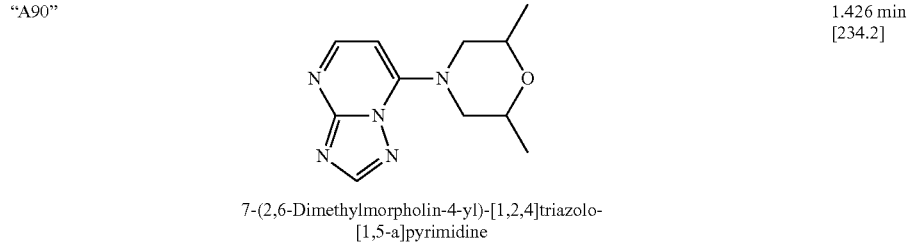<br>7-(2,6-Dimethylmorpholin-4-yl)-[1,2,4]triazolo-[1,5-a]pyrimidine | | 1.426 min [234.2] |

$^1$H NMR (500 MHz, d$_6$-DMSO) δ [ppm] 8.51 (s, 1H), 8.48 (d, J = 5.5, 1H), 6.70 (d, J = 5.5, 1H), 4.55 (d, J = 12.6, 2H), 3.79 (m, 2H), 2.81 (dd, J = 12.6, 10.6, 2H), 1.17 (d, J = 6.2, 6H)

| Compound No. | Structure and/or name | M.p. [°C.] | HPLC-MS; rt; [M + H⁺]$ |
|---|---|---|---|
| "A91" | 4-Morpholin-4-yl-7H-pyrrolo[2,3-d]pyrimidine | | 0.923 min [205.2] |

¹H NMR (500 MHz, d₆-DMSO) δ [ppm] 12.10 (br. s, 1H), 8.25 (s, 1H), 7.30 (dd, J = 3.3, 2.4, 1H), 6.82-6.68 (m, 1H), 3.97-3.82 (m, 4H), 3.82-3.67 (m, 4H)

| | | | |
|---|---|---|---|
| "A92" | N-[4-(Cyanodimethylmethyl)phenyl]-N-[1,2,4]-triazolo[1,5-a]pyrimidin-7-ylacetamide | | 1.622 min [321.2] |
| "A93" | tert-Butyl ((R)-1-(1H-imidazol-4-ylmethyl)-2-oxo-2-{8-[(R)-1-(9H-purin-6-yl)pyrrolidin-2-yl-methoxy]-3,4-dihydro-1H-isoquinolin-2-yl}ethyl)-carbamate | | 1.587 min [588.3] |

TABLE 1

Inhibition of MetAP-2 IC50 of compounds according to the invention

| Compound No. | IC₅₀ enzyme |
|---|---|
| "A1" | A |
| "A2" | C |
| "A3" | |
| "A4" | C |
| "A5" | A |
| "A6" | |
| "A7" | C |
| "A8" | A |
| "A9" | A |
| "A10" | A |
| "A11" | A |
| "A12" | A |
| "A13" | A |
| "A14" | C |
| "A15" | A |
| "A16" | A |
| "A17" | A |
| "A18" | A |
| "A19" | A |
| "A20" | A |
| "A21" | A |
| "A22" | A |
| "A23" | A |
| "A24" | A |
| "A25" | B |
| "A26" | A |
| "A27" | A |
| "A28" | B |
| "A29" | A |
| "A30" | |
| "A31" | A |
| "A32" | A |

TABLE 1-continued

Inhibition of MetAP-2 IC50 of compounds according to the invention

| Compound No. | $IC_{50}$ enzyme |
|---|---|
| "A33" | A |
| "A34" | A |
| "A35" | A |
| "A36" | A |
| "A37" | A |
| "A38" | A |
| "A39" | A |
| "A40" | A |
| "A41" | A |
| "A42" | A |
| "A43" | A |
| "A44" | A |
| "A45" | A |
| "A46" | A |
| "A47" | C |
| "A48" | B |
| "A49" | B |
| "A50" | A |
| "A51" | A |
| "A52" | A |
| "A53" | A |
| "A54" | A |
| "A55" | A |
| "A56" | B |
| "A57" | C |
| "A58" | C |
| "A59" | A |
| "A60" | C |
| "A61" | A |
| "A62" | A |
| "A63" | A |
| "A64" | A |
| "A65" | C |
| "A66" | A |
| "A67" | A |
| "A68" | A |
| "A69" | A |
| "A70" | A |
| "A71" | A |
| "A72" | A |
| "A73" | A |
| "A74" | A |
| "A75" | A |
| "A76" | A |
| "A77" | B |
| "A78" | B |
| "A79" | A |
| "A80" | B |
| "A81" | A |
| "A82" | A |
| "A83" | A |
| "A84" | B |

$IC_{50}$:
10 nM – 1 µM = A
1 µM – 10 µM = B
> 10 µM = C

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound of the formula I

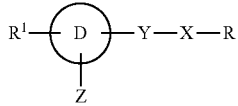    I in which

denotes pyrrolidinyl, imidazolinyl, pyrazolyl, 2-oxa-5-aza-bicyclo [2.2.1]hept-5-yl, morpholinyl or N, Z denotes imidazopyrimidinyl, triazolopyrimidinyl or pyrrolo-pyrimidinyl,
where Z is bonded to a nitrogen of the radical D, Y denotes $(CH_2)_n$ or is absent, X denotes $O(CH_2)_r$, NH, NA, OC(=O), NHSO$_2$ or is absent, $R^1$ denotes H, A or COA, R denotes Het, Het denotes quinolinyl, isoquinolinyl or isoindolyl, each of which is mono-, di- or trisubstituted by Hal, A, $(CH_2)_mOR^6$, $(CH2)_mN(R^6)_2$, $(CH_2)_mCN$, $(CH_2)_mCOOR^6$, $CONH(CH_2)_mCOOH$, $CONH(CH_2)_mHet^2$, $CO(CH_2)_mN(R^6)_2$, $CO(CH_2)_mNH(CH_2)_nCOOA$, $(CH_2)_nCONH(CH_2)_mAr^1$, $COCH[(CH_2)_mCONH_2]NH_2$, $COCH[(CH_2)_mCONH_2]NHCOOA$, $COCH[(CH_2)_mHet^2]NHCOOA$, $COCH(NHCOA)CH_2CONH_2$, $(CH_2)_mNHCOOA$, $COCH[(CH_2)_mCN]NHCOOA$, $COO(CH_2)_mCN$, $COO(CH_2)_mN(R^6)_2$, $CO(CH_2)_mCON(R^6)_2$, $COR^6$, $COHet^2$, $O(CH_2)_mAr^1$ and/or =O, Het$^2$ denotes imidazolyl, indolyl, isoxazolyl, pyridazinyl, pyrazolyl, benzimidazolyl, pyridyl, dibenzofuranyl, carbazolyl, benzo-furanyl, isoindolyl, quinazolinyl, quinoxalinyl, pyrimidinyl, indazolyl, furyl, thienyl, pyrrolyl, oxazolyl, thiazolyl, triazolyl, tetrazolyl, thiadiazole, benzothiazolyl, imidazo[1,2-α]pyridinyl or 1,3-benzodioxolyl, $R^6$ denotes H or alkyl having 1-6 C atoms, $Ar^1$ denotes phenyl which is unsubstituted or mono-, di- or trisubstituted by Hal and/or $SO_2NH_2$, A denotes unbranched or branched alkyl having 1-10 C atoms, in which 1-7 H atoms may be replaced by F, Cl, Br and/or OH, or
cyclic alkyl having 3-7 C atoms, Hal denotes F, Cl, Br or I, m denotes 0, 1, 2, 3, 4, 5 or 6, n denotes 1 or 2, r denotes 0, 1 or 2, and pharmaceutically usable salts, tautomers and stereoisomers thereof, including mixtures thereof in all ratios.

2. A compound, selected from the group of the following compounds:

| Compound No. | Name and/or structure |
|---|---|
| "A5" | 5-((R)-1-[1,2,4]Triazolo[1,5-a]pyrimidin-7-ylpyrrolidin-2-ylmethoxy)quinoline |
| "A8" | 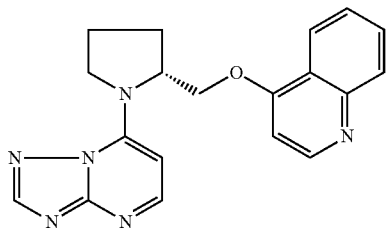 [SMILES: c1ccc2c(OC[C@H]3CCCN3c3ccnc4ncnn34)ccnc2c1]<br>4-((R)-1-[1,2,4]Triazolo[1,5-a]pyrimidin-7-ylpyrrolidin-2-ylmethoxy)quinoline |
| "A9" | 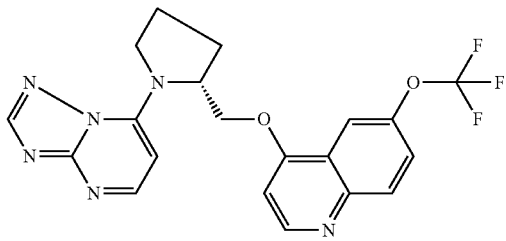 [SMILES: FC(F)(F)Oc1ccc2nccc(OC[C@H]3CCCN3c3ccnc4ncnn34)c2c1]<br>4-((R)-1-[1,2,4]Triazolo[1,5-a]pyrimidin-7-ylpyrrolidin-2-ylmethoxy)-6-trifluoromethoxyquinoline |

| Compound No. | Name and/or structure |
|---|---|
| "A10" | 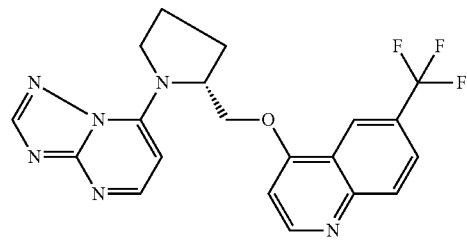 [SMILES: FC(F)(F)c1ccc2nccc(OC[C@H]3CCCN3c3ccnc4ncnn34)c2c1]<br>4-((R)-1-[1,2,4]Triazolo[1,5-a]pyrimidin-7-ylpyrrolidin-2-yl-methoxy)-6-trifluoromethylquinoline |
| "A11" | 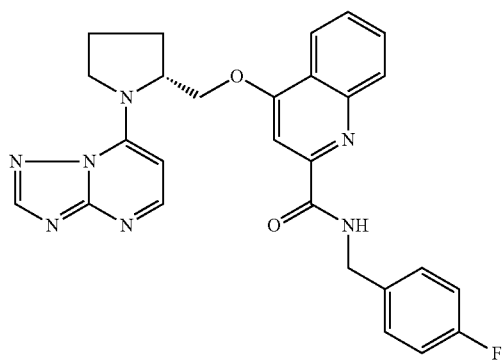 [SMILES: O=C(NCc1ccc(F)cc1)c1cc(OC[C@H]2CCCN2c2ccnc3ncnn23)c2ccccc2n1]<br>N-4-Fluorobenzyl-4-((R)-1-[1,2,4]triazolo[1,5-a]pyrimidin-7-yl-pyrrolidin-2-ylmethoxy)quinoline-2-carboxamide |
| "A12" | 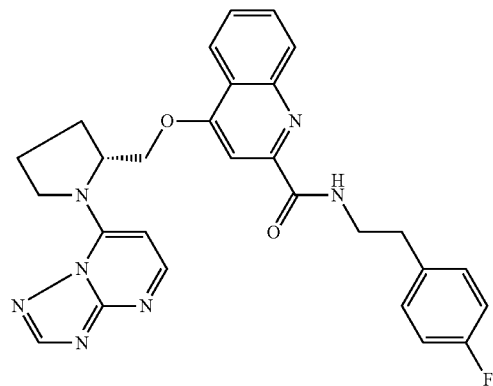 [SMILES: O=C(NCCc1ccc(F)cc1)c1cc(OC[C@H]2CCCN2c2ccnc3ncnn23)c2ccccc2n1]<br>N-[2-(4-Fluorophenyl)ethyl]-4-((R)-1-[1,2,4]triazolo[1,5-a]-pyrimidin-7-ylpyrrolidin-2-ylmethoxy)quinoline-2-carboxamide |
| "A13" | 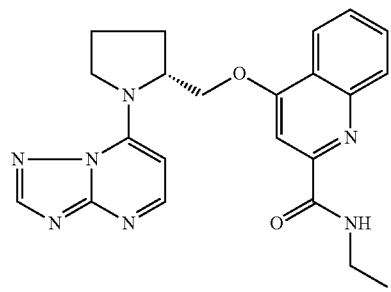 [SMILES: CCNC(=O)c1cc(OC[C@H]2CCCN2c2ccnc3ncnn23)c2ccccc2n1]<br>N-Ethyl-4-((R)-1-[1,2,4]triazolo[1,5-a]pyrimidin-7-ylpyrrolidin-2-ylmethoxy)quinoline-2-carboxamide |

| Compound No. | Name and/or structure |
|---|---|
| "A16" | 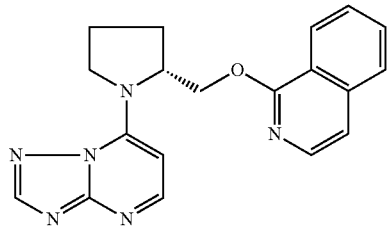 [SMILES: c1ccc2c(OC[C@H]3CCCN3c3ccnc4ncnn34)nccc2c1]
1-((R)-1-[1,2,4]Triazolo[1,5-a]pyrimidin-7-ylpyrrolidin-2-yl-methoxy)isoquinoline |
| "A17" | 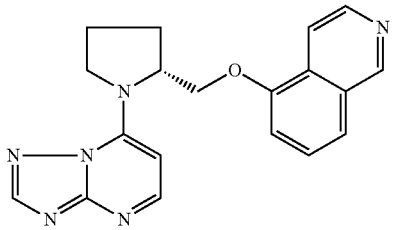 [SMILES: c1cc(OC[C@H]2CCCN2c2ccnc3ncnn23)c2ccncc2c1]
5-((R)-1-[1,2,4]Triazolo[1,5-a]pyrimidin-7-ylpyrrolidin-2-yl-methoxy)isoquinoline |
| "A18" | 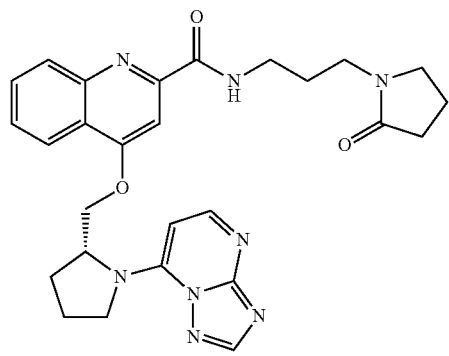 [SMILES: O=C(NCCCN1CCCC1=O)c1cc(OC[C@H]2CCCN2c2ccnc3ncnn23)c2ccccc2n1]
N-[3-(2-Oxopyrrolidin-1-yl)propyl]-4-((R)-1-[1,2,4]triazolo-[1,5-a]pyrimidin-7-ylpyrrolidin-2-ylmethoxy)quinoline-2-carboxamide |
| "A22" | 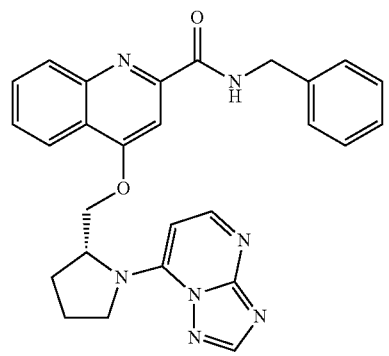 [SMILES: O=C(NCc1ccccc1)c1cc(OC[C@H]2CCCN2c2ccnc3ncnn23)c2ccccc2n1]
N-Benzyl-4-((R)-1-[1,2,4]triazolo[1,5-a]pyrimidin-7-yl-pyrrolidin-2-ylmethoxy)quinoline-2-carboxamide |

-continued

| Compound No. | Name and/or structure |
|---|---|
| "A23" | 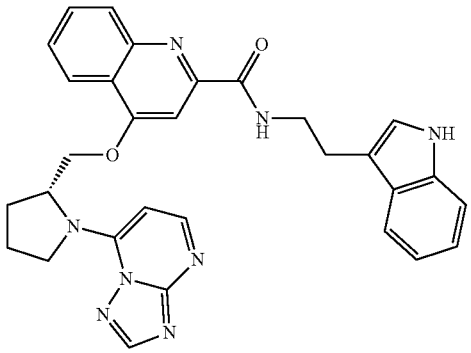 [SMILES: O=C(NCCc1c[nH]c2ccccc12)c1cc(OC[C@H]2CCCN2c2ccnc3ncnn23)c2ccccc2n1]<br>N-[2-(1H-Indol-3-yl)ethyl]-4-((R)-1-[1,2,4]triazolo-[1,5-a]pyrimidin-7-ylpyrrolidin-2-ylmethoxy)quinoline-2-carboxamide |
| "A24" | 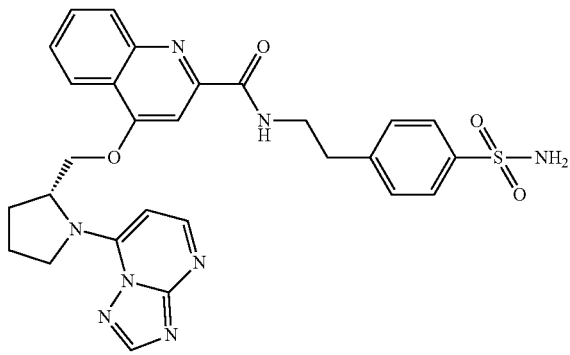 [SMILES: NS(=O)(=O)c1ccc(CCNC(=O)c2cc(OC[C@H]3CCCN3c3ccnc4ncnn34)c3ccccc3n2)cc1]<br>N-[2-(4-Sulfamoylphenyl)ethyl]-4-((R)-1-[1,2,4]triazolo-[1,5-a]pyrimidin-7-ylpyrrolidin-2-ylmethoxy)quinoline-2-carboxamide |
| "A25" | 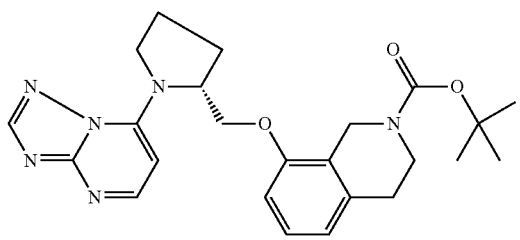 [SMILES: CC(C)(C)OC(=O)N1CCc2cccc(OC[C@H]3CCCN3c3ccnc4ncnn34)c2C1]<br>tert-Butyl 8-((R)-1-[1,2,4]triazolo[1,5-a]pyrimidin-7-yl-pyrrolidin-2-ylmethoxy)-3,4-dihydro-1H-isoquinoline-2-carboxylate |
| "A27" | 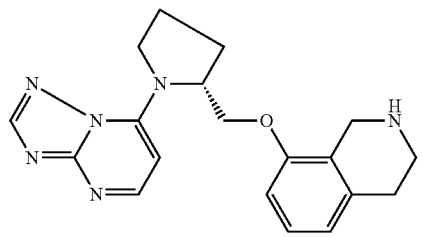 [SMILES: c1cc2c(c(OC[C@H]3CCCN3c3ccnc4ncnn34)c1)CNCC2]<br>8-((R)-1-[1,2,4]Triazolo[1,5-a]pyrimidin-7-ylpyrrolidin-2-yl-methoxy)-1,2,3,4-tetrahydroisoquinoline |

| Compound No. | Name and/or structure |
|---|---|
| "A28" | 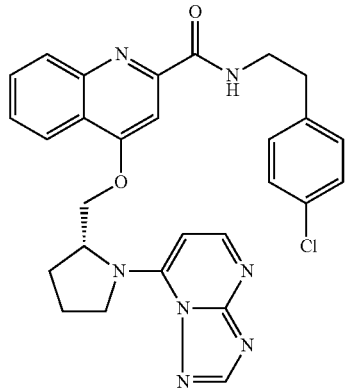 [SMILES: O=C(NCCc1ccc(Cl)cc1)c1cc(OC[C@H]2CCCN2c2ccnc3ncnn23)c2ccccc2n1]<br>N-[2-(4-Chlorophenyl)ethyl]-4-((R)-1-[1,2,4]triazolo[1,5-a]-pyrimidin-7-ylpyrrrolidin-2-ylmethoxy)quinoline-2-carboxamide |
| "A29" | 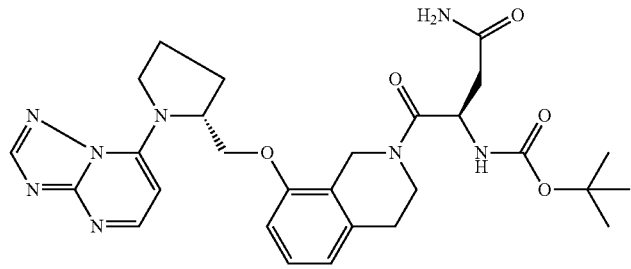 [SMILES: CC(C)(C)OC(=O)N[C@H](CC(N)=O)C(=O)N1CCc2cccc(OC[C@H]3CCCN3c3ccnc4ncnn34)c2C1]<br>tert-Butyl{(R)-1-carbamoylmethyl-2-oxo-2-[8-((R)-1-[1,2,4]-triazolo[1,5-a]pyrimidin-7-ylpyrrolidin-2-ylmethoxy)-3,4-dihydro-1H-isoquinolin-2-yl]ethyl}carbamate |
| "A30" | 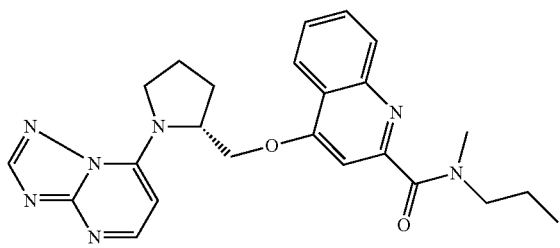 [SMILES: CCCN(C)C(=O)c1cc(OC[C@H]2CCCN2c2ccnc3ncnn23)c2ccccc2n1]<br>N-Ethylpropyl-4-((R)-1-[1,2,4]triazolo[1,5-a]pyrimidin-7-yl-pyrrolidin-2-ylmethoxy)quinoline-2-carboxamide |
| "A31" | 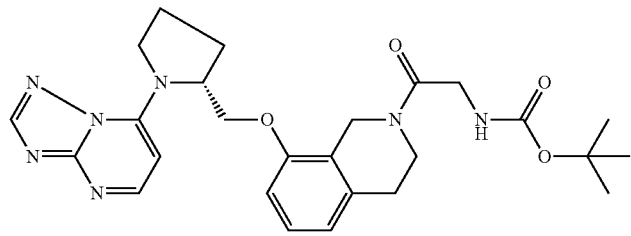 [SMILES: CC(C)(C)OC(=O)NCC(=O)N1CCc2cccc(OC[C@H]3CCCN3c3ccnc4ncnn34)c2C1]<br>tert-Butyl {2-oxo-2-[8-((R)-1-[1,2,4]triazolo[1,5-a]pyrimidin-7-ylpyrrolidin-2-ylmethoxy)-3,4-dihydro-1H-isoquinolin-2-yl]-ethyl}carbamate |

| Compound No. | Name and/or structure |
|---|---|
| "A32" | 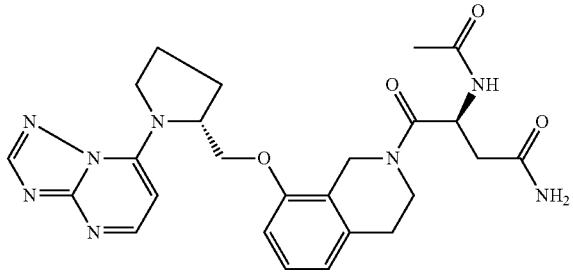 [SMILES: CC(=O)N[C@@H](CC(N)=O)C(=O)N1CCc2cccc(OC[C@H]3CCCN3c3ccnc4ncnn34)c2C1]<br>(S)-3-Acetylamino-4-oxo-4-[8-((R)-1-[1,2,4]triazolo[1,5-a]-pyrimidin-7-ylpyrrolidin-2-ylmethoxy)-3,4-dihydro-1H-isoquinolin-2-yl]butyramide |
| "A33" | 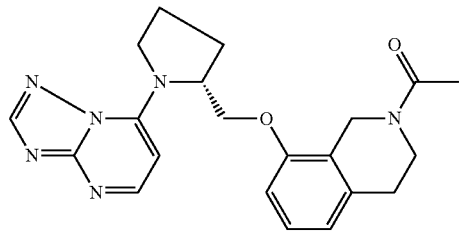 [SMILES: CC(=O)N1CCc2cccc(OC[C@H]3CCCN3c3ccnc4ncnn34)c2C1]<br>1-[8-((R)-1-[1,2,4]Triazolo[1,5-a]pyrimidin-7-ylpyrrolidin-2-yl-methoxy)-3,4-dihydro-1H-isoquinolin-2-yl]ethanone |
| "A34" | 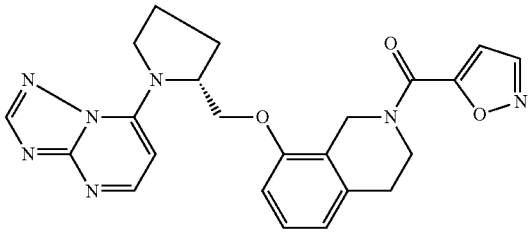 [SMILES: O=C(c1ccno1)N1CCc2cccc(OC[C@H]3CCCN3c3ccnc4ncnn34)c2C1]<br>Isoxazol-5-yl-[8-((R)-1-[1,2,4]triazolo[1,5-a]pyrimidin-7-yl-pyrrolidin-2-ylmethoxy)-3,4-dihydro-1H-isoquinolin-2-yl]-methanone |
| "A35" | 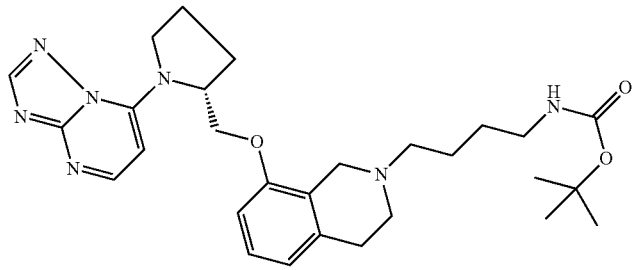 [SMILES: CC(C)(C)OC(=O)NCCCCN1CCc2cccc(OC[C@H]3CCCN3c3ccnc4ncnn34)c2C1]<br>tert-Butyl {4-[8-((R)-1-[1,2,4]triazolo[1,5-a]pyrimidin-7-yl-pyrrolidin-2-ylmethoxy)-3,4-dihydro-1H-isoquinolin-2-yl]-butyl}carbamate |

| Compound No. | Name and/or structure |
|---|---|
| "A36" | 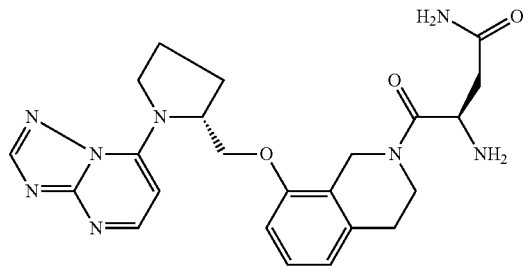 [SMILES: NC(=O)C[C@@H](N)C(=O)N1CCc2cccc(OC[C@H]3CCCN3c3ccnc4ncnn34)c2C1]<br>(R)-3-Amino-4-oxo-4-[8-((R)-1-[1,2,4]triazolo[1,5-a]pyrimidin-7-ylpyrrolidin-2-ylmethoxy)-3,4-dihydro-1H-isoquinolin-2-yl]-butyramide |
| "A37" | 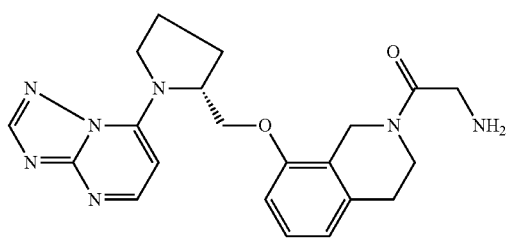 [SMILES: NCC(=O)N1CCc2cccc(OC[C@H]3CCCN3c3ccnc4ncnn34)c2C1]<br>2-Amino-1-[8-((R)-1-[1,2,4]triazolo[1,5-a]pyrimidin-7-yl-pyrrolidin-2-ylmethoxy)-3,4-dihydro-1H-isoquinolin-2-yl]-ethanone |
| "A38" | 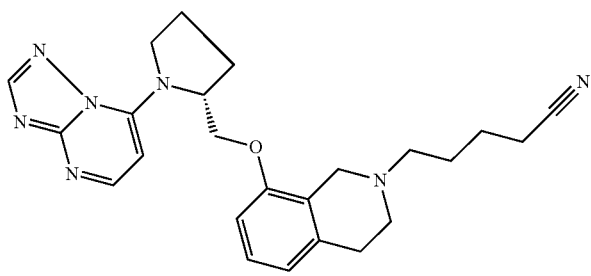 [SMILES: N#CCCCCN1CCc2cccc(OC[C@H]3CCCN3c3ccnc4ncnn34)c2C1]<br>5-[8-((R)-1-[1,2,4]Triazolo[1,5-a]pyrimidin-7-ylpyrrolidin-2-yl-methoxy)-3,4-dihydro-1H-isoquinolin-2-yl]pentanenitrile |
| "A39" | 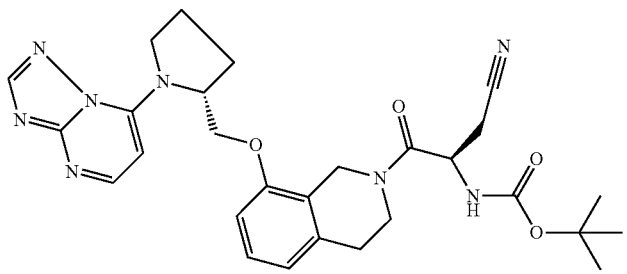 [SMILES: CC(C)(C)OC(=O)N[C@H](CC#N)C(=O)N1CCc2cccc(OC[C@H]3CCCN3c3ccnc4ncnn34)c2C1]<br>tert-Butyl {(R)-2-cyano-1-[8-((R)-1-[1,2,4]triazolo-[1,5-a]pyrimidin-7-ylpyrrolidin-2-ylmethoxy)-3,4-dihydro-1H-isoquinoline-2-carbonyl]ethyl}carbamate |

| Compound No. | Name and/or structure |
|---|---|
| "A40" | 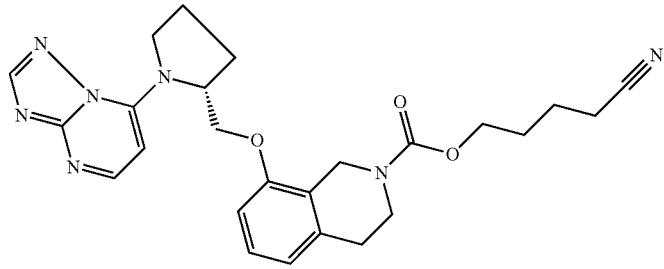 [SMILES: N#CCCCCOC(=O)N1CCc2cccc(OC[C@H]3CCCN3c3ccnc4ncnn34)c2C1]<br>4-Cyanobutyl 8-((R)-1-[1,2,4]triazolo[1,5-a]pyrimidin-7-yl-pyrrolidin-2-ylmethoxy)-3,4-dihydro-1H-isoquinoline-2-carboxylate |
| "A41" | 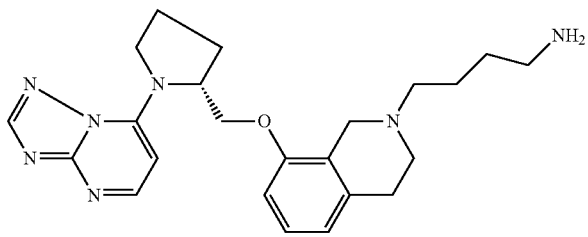 [SMILES: NCCCCN1CCc2cccc(OC[C@H]3CCCN3c3ccnc4ncnn34)c2C1]<br>4-[8-((R)-1-[1,2,4]Triazolo[1,5-a]pyrimidin-7-ylpyrrolidin-2-yl-methoxy)-3,4-dihydro-1H-isoquinolin-2-yl]butylamine |
| "A42" | 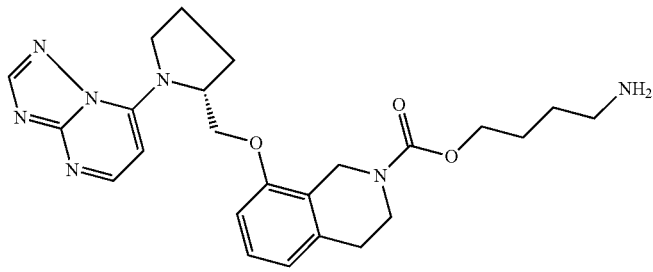 [SMILES: NCCCCOC(=O)N1CCc2cccc(OC[C@H]3CCCN3c3ccnc4ncnn34)c2C1]<br>4-Aminobutyl 8-((R)-1-[1,2,4]triazolo[1,5-a]pyrimidin-7-yl-pyrrolidin-2-ylmethoxy)-3,4-dihydro-1H-isoquinoline-2-carboxylate |
| "A46" | 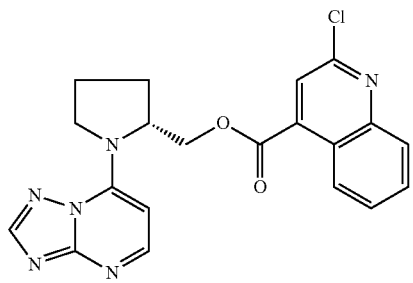 [SMILES: O=C(OC[C@H]1CCCN1c1ccnc2ncnn12)c1cc(Cl)nc2ccccc12]<br>(R)-1-[1,2,4]Triazolo[1,5-a]pyrimidin-7-ylpyrrolidin-2-ylmethyl 2-chloroquinoline-4-carboxylate |

| Compound No. | Name and/or structure |
|---|---|
| "A53" | 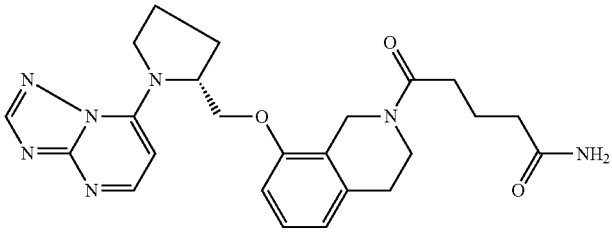<br>5-Oxo-5-[8-((R)-1-[1,2,4]triazolo[1,5-a]pyrimidin-7-yl-pyrrolidin-2-ylmethoxy)-3,4-dihydro-1H-isoquinolin-2-yl]-pentanamide |
| "A59" | 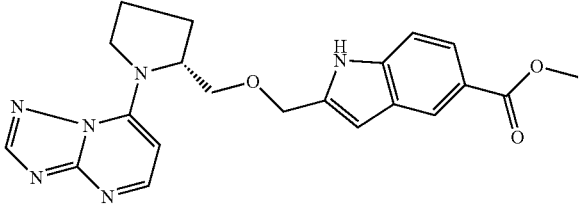 [SMILES: COC(=O)c1ccc2[nH]c(COC[C@H]3CCCN3c3ccnc4ncnn34)cc2c1]<br>Methyl 2-((R)-1-[1,2,4]triazolo[1,5-a]pyrimidin-7-ylpyrrolidin-2-ylmethoxymethyl)-1H-indole-5-carboxylate |
| "A75" | 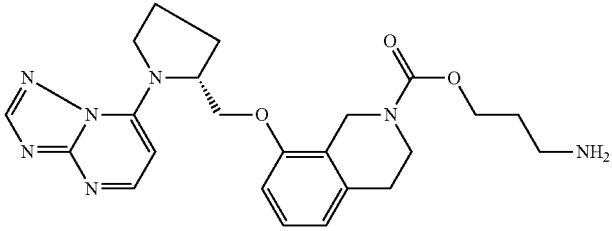 [SMILES: NCCCOC(=O)N1CCc2cccc(OC[C@H]3CCCN3c3ccnc4ncnn34)c2C1]<br>3-Aminopropyl 8-((R)-1-[1,2,4]triazolo[1,5-a]pyrimidin-7-yl-pyrrolidin-2-ylmethoxy)-3,4-dihydro-1H-isoquinoline-2-carboxylate |
| "A76" | 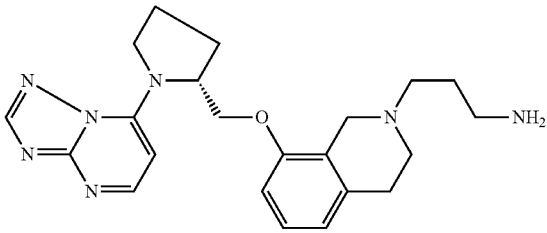 [SMILES: NCCCN1CCc2cccc(OC[C@H]3CCCN3c3ccnc4ncnn34)c2C1]<br>3-[8-((R)-1-[1,2,4]Triazolo[1,5-a]pyrimidin-7-ylpyrrolidin-2-yl-methoxy)-3,4-dihydro-1H-isoquinolin-2-yl]propylamine |
| "A77" | 7-[(R)-2-(Naphthalen-1-yloxymethyl)pyrrolidin-1-yl]-[1,2,4]-triazolo[1,5-a]-1,3,5-triazine |
| "A78" | 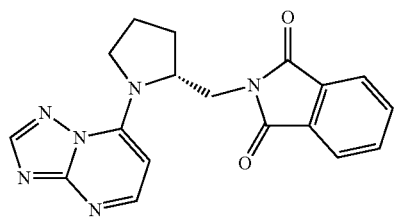 [SMILES: O=C1c2ccccc2C(=O)N1C[C@H]1CCCN1c1ccnc2ncnn12]<br>2-((R)-1-[1,2,4]Triazolo[1,5-a]pyrimidin-7-ylpyrrolidin-2-yl-methyl)isoindole-1,3-dione |

| Compound No. | Name and/or structure |
|---|---|
| "A81" | 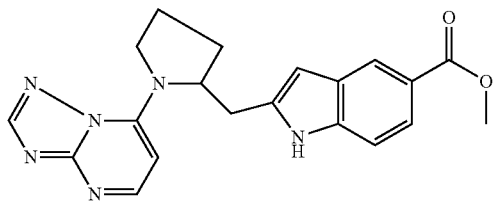 [SMILES: COC(=O)c1ccc2[nH]c(CC3CCCN3c3ccnc4ncnn34)cc2c1]<br>Methyl 2-(1-[1,2,4]triazolo[1,5-a]pyrimidin-7-ylpyrrolidin-2-yl-methyl-1H-indole-5-carboxylate |
| "A93" | 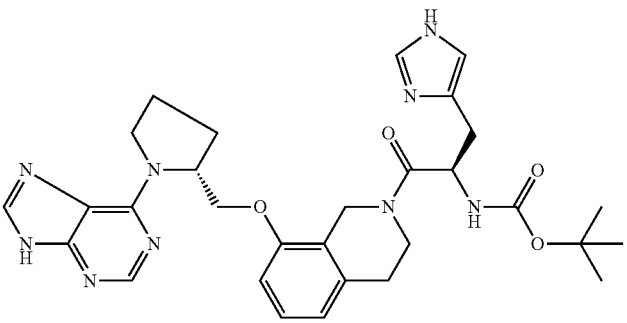 [SMILES: CC(C)(C)OC(=O)N[C@H](Cc1c[nH]cn1)C(=O)N1CCc2cccc(OC[C@H]3CCCN3c3ncnc4[nH]cnc34)c2C1]<br>tert-Butyl ((R)-1-(1H-imidazol-4-ylmethyl)-2-oxo-2-{8-[(R)-1-(9H-purin-6-yl)pyrrolidin-2-ylmethoxy]-3,4-dihydro-1H-isoquinolin-2-yl}ethyl)carbamate | and pharmaceutically usable salts, tautomers and stereoisomers thereof, including mixtures thereof in all ratios.

3. A composition comprising at least one compound of the formula I according to claim 1 and/or pharmaceutically usable salts, tautomers and stereoisomers thereof, including mixtures thereof in all ratios, and optionally excipients and/or adjuvants.

4. A composition comprising at least one compound according to claim 2 and/or pharmaceutically usable salts, tautomers and stereoisomers thereof, including mixtures thereof in all ratios, and optionally excipients and/or adjuvants.

\* \* \* \* \*